United States Patent
Greenberg et al.

(10) Patent No.: US 11,627,664 B2
(45) Date of Patent: Apr. 11, 2023

(54) FLEXIBLE CIRCUIT ELECTRODE ARRAY AND METHOD OF MANUFACTURING THE SAME

(71) Applicant: Second Sight Medical Products, Inc., Sylmar, CA (US)

(72) Inventors: Robert Jay Greenberg, Los Angeles, CA (US); Neil Hamilton Talbot, La Crescenta, CA (US); Jordan Matthew Neysmith, Mountain View, CA (US); Jerry Ok, Granada Hills, CA (US)

(73) Assignee: Cortigent, Inc., Sylmr, CA (US)

( * ) Notice: Subject to any disclaimer, the term of this patent is extended or adjusted under 35 U.S.C. 154(b) by 82 days.

(21) Appl. No.: 16/425,809

(22) Filed: May 29, 2019

(65) Prior Publication Data

US 2019/0297729 A1    Sep. 26, 2019

Related U.S. Application Data

(62) Division of application No. 13/668,137, filed on Nov. 2, 2012, now Pat. No. 10,362,681, which is a division
(Continued)

(51) Int. Cl.
*H05K 3/06* (2006.01)
*A61N 1/05* (2006.01)
(Continued)

(52) U.S. Cl.
CPC .............. *H05K 3/06* (2013.01); *A61N 1/0543* (2013.01); *H05K 1/0346* (2013.01);
(Continued)

(58) Field of Classification Search
CPC .......... H05K 3/06; H05K 3/0041; H05K 3/28; H05K 3/381; H05K 3/288; H05K 1/118;
(Continued)

(56) References Cited

U.S. PATENT DOCUMENTS 4,325,780 A    4/1982 Schulz
4,573,481 A    3/1986 Bullara
(Continued)

FOREIGN PATENT DOCUMENTS

JP    2004004947 A  *  1/2004
JP    2004195206 A  *  7/2004
(Continued)

OTHER PUBLICATIONS

Egitto, et al. Plasma etching of organic materials, J. Vac. Sci. Technol. B 3(3), May/Jun. 1985, pp. 893-904.
(Continued)

*Primary Examiner* — Livius R. Cazan
(74) *Attorney, Agent, or Firm* — Scott Dunbar

(57) ABSTRACT

A method for manufacturing a flexible circuit electrode array, comprising:
a) depositing a metal trace layer containing a base coating layer, a conducting layer and a top coating layer on the insulator polymer base layer;
b) applying a layer of photoresist on the metal trace layer and patterning the metal trace layer and forming metal traces on the insulator polymer base layer;
c) activating the insulator polymer base layer and depositing a top insulator polymer layer and forming one single insulating polymer layer with the base insulator polymer layer;
d) applying a thin metal layer and a layer of photoresist on the surface of the insulator polymer layer and selective etching the insulator layer and the top coating layer to obtain at least one via; and
e) filling the via with electrode material.

A layer of polymer is laid down. A layer of metal is applied to the polymer and patterned to create electrodes and leads for those electrodes. A second layer of polymer is applied
(Continued)

over the metal layer and patterned to leave openings for the electrodes, or openings are created later by means such as laser ablation. Hence the array and its supply cable are formed of a single body. Alternatively, multiple alternating layers of metal and polymer may be applied to obtain more metal traces within a given width.

The method provides an excellent adhesion between the polymer base layer and the polymer top layer and insulation of the trace metals and electrodes.

4 Claims, 12 Drawing Sheets

Related U.S. Application Data of application No. 11/926,498, filed on Oct. 29, 2007, now Pat. No. 8,322,027, which is a division of application No. 11/545,354, filed on Oct. 10, 2006, now Pat. No. 7,877,866.

(60) Provisional application No. 60/730,916, filed on Oct. 26, 2005.

(51) Int. Cl.
| | |
|---|---|
| *H05K 3/00* | (2006.01) |
| *H05K 3/28* | (2006.01) |
| *H05K 3/38* | (2006.01) |
| *H05K 1/11* | (2006.01) |
| *H05K 1/03* | (2006.01) |

(52) U.S. Cl.
CPC ......... *H05K 1/0393* (2013.01); *H05K 3/0041* (2013.01); *H05K 3/28* (2013.01); *H05K 3/381* (2013.01); *H05K 1/118* (2013.01); *H05K 3/388* (2013.01); *H05K 2201/0154* (2013.01); *H05K 2201/0317* (2013.01); *H05K 2203/0554* (2013.01); *H05K 2203/0789* (2013.01); *H05K 2203/0793* (2013.01); *H05K 2203/095* (2013.01); *H05K 2203/1163* (2013.01); *Y10T 29/49124* (2015.01); *Y10T 29/49147* (2015.01); *Y10T 29/49155* (2015.01)

(58) Field of Classification Search
CPC .. H05K 1/0393; H05K 1/0346; A61N 1/0543; A61N 1/36046
See application file for complete search history.

(56) References Cited

U.S. PATENT DOCUMENTS

| | | | |
|---|---|---|---|
| 4,628,933 | A | 12/1986 | Michelson |
| 4,720,915 | A | 1/1988 | Kennedy et al. |
| 4,729,061 | A | 3/1988 | Brown |
| 4,837,049 | A | 6/1989 | Byers et al. |
| 5,109,844 | A | 5/1992 | de Juan, Jr. et al. |
| 5,118,385 | A * | 6/1992 | Kumar ................ H01L 21/4857 216/105 |
| 5,151,304 | A * | 9/1992 | Lee .......................... B05D 3/10 204/192.1 |
| 5,215,088 | A | 6/1993 | Norman et al. |
| 5,306,670 | A | 4/1994 | Mowatt et al. |
| 5,429,709 | A | 7/1995 | Mizutani et al. |
| 5,470,693 | A | 11/1995 | Sachdev et al. |
| 5,476,494 | A * | 12/1995 | Edell .................... A61N 1/0543 600/383 |
| 5,531,022 | A | 7/1996 | Beaman et al. |
| 5,680,701 | A | 10/1997 | Sippel |
| 5,832,598 | A | 11/1998 | Greenman et al. |
| 5,863,405 | A | 1/1999 | Miyeshita |
| 5,935,155 | A | 8/1999 | Humayun et al. |
| 6,048,430 | A | 4/2000 | Johnston |
| 6,121,553 | A | 9/2000 | Shinada et al. |
| 6,200,407 | B1 | 3/2001 | Wieloch et al. |
| 6,400,989 | B1 | 6/2002 | Eckmiller |
| 6,458,157 | B1 | 10/2002 | Suaning |
| 6,803,528 | B1 | 10/2004 | Koyanagi |
| 2002/0056192 | A1 | 5/2002 | Suwa et al. |
| 2003/0029636 | A1 | 2/2003 | Carpenter et al. |
| 2003/0091800 | A1 | 5/2003 | Zhang |
| 2003/0195601 | A1* | 10/2003 | Hung ................... A61N 1/0551 607/116 |
| 2004/0016570 | A1 | 1/2004 | Yamamoto et al. |
| 2004/0049912 | A1 | 3/2004 | Akagawa et al. |
| 2004/0177499 | A1 | 9/2004 | Eldridge et al. |
| 2004/0209439 | A1 | 10/2004 | Haba |
| 2004/0220667 | A1* | 11/2004 | Gelfandbein ........ C23C 14/0605 623/6.56 |
| 2005/0155788 | A1 | 7/2005 | Benson |
| 2005/0189139 | A1 | 9/2005 | Stole |
| 2005/0205294 | A1 | 9/2005 | Yamashita et al. |
| 2013/0319971 | A1 | 12/2013 | Greenberg et al. |

FOREIGN PATENT DOCUMENTS

| | | |
|---|---|---|
| KR | 2003035738 | 5/2003 |
| KR | 20030035738 A * | 5/2003 |

OTHER PUBLICATIONS

Lee, et al. Surface modification of BPDA-PDA Polyimide, American Chemical Society, vol. 7, No. 11, 1991, pp. 2450-2453.

* cited by examiner

FLEXIBLE CIRCUIT ELECTRODE ARRAY AND METHOD OF MANUFACTURING THE SAME

CROSS-REFERENCE TO RELATED APPLICATIONS

This application is a divisional application of U.S. patent application Ser. No. 13/668,137, filed Nov. 2, 2012, for Flexible Circuit Electrode Array and Method of Manufacturing the Same, which is a divisional application of U.S. patent application Ser. No. 11/926,498, filed Nov. 2, 2012 for Flexible Circuit Electrode Array and Method of Manufacturing the Same, which is a divisional application of U.S. patent application Ser. No. 11/545,354, filed Oct. 10, 2006 for Flexible Circuit Electrode Array and Method of Manufacturing the Same, which claims the benefit of U.S. Provisional Application No. 60/730,916, filed Oct. 26, 2005, Flexible Circuit Electrode Array and Method of Manufacturing the Same, the disclosures of which are incorporated herein by reference.

STATEMENT REGARDING FEDERALLY SPONSORED RESEARCH OR DEVELOPMENT

This invention was made with government support under grant No. R24EY12893-01, which has been awarded by the National Institutes of Health. The government has certain rights in the invention.

FIELD OF THE INVENTION

The present invention is generally directed to a flexible circuit electrode array especially for biomedical implants, especially implantable medical devices, such as a retinal prosthesis and a method of manufacturing the flexible circuit electrode array.

DESCRIPTION OF THE RELATED ART

In U.S. Pat. No. 3,699,970 "Striate Cortex Stimulator" to Giles Skey Brindley et al. an implantable device is disclosed comprising a plurality of electrodes for stimulating the striate cortex.

In U.S. Pat. No. 4,487,652 "Slope Etch of Polyimide" to Carl W. Amgren a semiconductor having an insulating layer overlying a metal layer is disclosed, wherein the insulator comprises an upper oxide layer, an intermediate polyimide layer, and a lower oxide layer in contact with the metal layer, a method for etching a via from an upper surface of the polyimide layer to the metal layer comprising the steps of applying photoresist; etching an opening from an upper surface of the photoresist layer to the upper oxide layer at a location for forming the via so that an upper surface of the upper oxide layer is exposed at the via location; heating the photoresist to cause a more gradual slope of the photoresist layer from the upper surface of the upper oxide layer at the via location to the upper surface of the photoresist layer; applying reactive ion etchant with a predetermined selectivity between photoresist and oxide to transfer the slope of the photoresist layer to the upper oxide layer at a predetermined ratio; and applying a reactive ion etchant with a predetermined selectivity between oxide and polyimide to transfer the slope of the upper oxide layer to the polyimide layer at a predetermined ratio, whereby the lower oxide layer is simultaneously etched to expose the metal layer at the via location.

In U.S. Pat. No. 4,573,481 "Implantable Electrode Array" to Leo A. Bullara an electrode assembly for surgical implantation on a nerve of the peripheral nerve system is disclosed.

In U.S. Pat. No. 4,628,933 "Method and Apparatus for Visual Prosthesis" to Robin P. Michelson a visual prosthesis for implantation in the eye in the optical pathway thereof is disclosed.

In U.S. Pat. No. 4,837,049 "Method of Making an Electrode Array" to Charles L. Byers et al. a very small electrode array which penetrates nerves for sensing electrical activity therein or to provide electrical stimulation is disclosed.

In U.S. Pat. No. 4,996,629 "Circuit Board with Self-Supporting Connection Between Sides" to Robert A. Christiansen et al. a copper supporting sheet is disclosed having vias for connecting semiconductor chips to surface mount components. A laminate of polyimide has vias corresponding to the supporting layer vias with copper covering those vias.

In U.S. Pat. No. 5,108,819 "Thin Film Electrical Component" to James W. Heller a thin film electrical component is disclosed comprising a rigid glass carrier plate, a substrate bonded to the rigid glass carrier plate, the substrate comprising a polyimide establishing a bond with the rigid glass carrier plate that is broken upon immersion of the substrate and the rigid glass carrier plate in one of a hot water bath or a warm temperature physiologic saline bath to release the polymer from attachment to the rigid glass carrier plate, and means for providing an electrical circuit, the providing means being bonded to the substrate and undisrupted during release of the substrate from attachment to the rigid glass carrier plate.

In U.S. Pat. No. 5,109,844 "Retinal Microstimulation" to Eugene de Juan Jr. et al. a method for stimulating a retinal ganglion cell in a retina without penetrating the retinal basement membrane at the surface of the retina is disclosed.

In U.S. Pat. No. 5,178,957 "Noble Metal-Polymer Composites and Flexible Thin-Film Conductors Prepared Therefrom" to Vasant V. Kolpe a composite article is disclosed comprising a polymeric support selected from the group consisting of a polyimide, polyethylene terephthalate, and polyester-ether block copolymer having a noble metal deposited directly onto at least one surface, wherein the deposited metal exhibits a peel force of at least about 0.05 kg per millimeter width after a 24 hour boiling saline treatment.

In U.S. Pat. No. 5,215,088 "Three-Dimensional Electrode Device" to Richard A. Norman et al. a three-dimensional electrode device for placing electrodes in close proximity to a cell lying at least about 1000 microns below a tissue surface is disclosed.

In U.S. Pat. No. 5,935,155 "Visual Prosthesis and Method of Using Same" to Mark S. Humayun et al. a visual prosthesis is disclosed comprising a camera for receiving a visual image and generating a visual signal output, retinal tissue stimulation circuitry adapted to be operatively attached to the user's retina, and wireless communication circuitry for transmitting the visual signal output to the retinal tissue stimulation circuitry within the eye.

In U.S. Pat. No. 6,071,819 "Flexible Skin Incorporating MEMS Technology" to Yu-Chong Tai a method of manufacturing a flexible microelectronic device is disclosed comprising first etching a lower side of a wafer using a first caustic agent; depositing a first layer of aluminum on an upper side of the wafer; patterning the first layer of aluminum; depositing a first layer of polyimide on the upper side of the wafer, covering the first layer of aluminum; depositing a second layer of aluminum on the upper side of the wafer, covering the first layer of polyimide; depositing a second layer of polyimide on the upper side of the wafer, covering the second layer of aluminum; depositing a third layer of aluminum on the lower side of the wafer; patterning the third layer of aluminum; second etching the lower side of the wafer using the third layer of aluminum as a mask and the first layer of aluminum as an etch stop and using a less caustic agent than the first caustic agent, such that the wafer is divided into islands with gaps surrounding each island; and depositing a third layer of polyimide on the lower side of the wafer, such that the gaps are at least partially filled.

In U.S. Pat. No. 6,324,429 "Chronically Implantable Retinal Prosthesis" to Doug Shire et al. an apparatus is disclosed which is in contact with the inner surface of the retina and electrically stimulates at least a portion of the surface of the retina.

In U.S. Pat. No. 6,374,143 "Modiolar Hugging Electrode Array" to Peter G. Berrang et al. a cochlear electrode array for stimulating auditory processes is disclosed.

In U.S. Pat. No. 6,847,847 "Retina Implant Assembly and Methods for Manufacturing the Same" to Wilfried Nisch et al. a retina implant is disclosed comprising a chip in subretinal contact with the retina and a receiver coil for inductively coupling electromagnetic energy.

In US Patent Application No. 20010037061 A1, "Microcontact structure for neuroprostheses for implantation on nerve tissue and method therefore" to Rolf Eckmiller et al. a four layer microcontact structure is disclosed in which the active connection between the microcontact structure and the nerve tissue is brought about by electrical stimulation. The layer adjacent to the nerve tissue to be stimulated is composed of the polymer polyimide and contains penetrating electrodes made of platinum which form the adjoining layer. There follows a further layer of the polyimide and a layer of the polymer polyurethane. Polyurethane has the property of thermal expansion relative to polyimide.

In US Patent Application No. 2003/0158588 A1 "Minimal Invasive Retinal Prosthesis" to John F. Rizzo et al. a retinal prosthesis is disclosed comprising an RF coil attached to the outside of and moving with an eye to receive power from an external power source; electronic circuitry attached to and moving with the eye and electrically connected to the RF coil; a light sensitive array electrically connected to the electronic circuitry and located within the eye for receiving incident light and for generating an electrical signal in response to the incident light; and a stimulating array abutting a retina of the eye and electrically connected to the electronic circuitry to stimulate retinal tissue in response to the electrical signal from the light sensitive array. A supporting silicone substrate has a polyimide layer spun onto its surface and cured. The copper or chrome/gold conducting layer is then added and patterned using wet chemical etching or a photoresist lift-off process. Next, a second polyimide layer is spun on, and the regions where circuit components are to be added are exposed by selective dry etching or laser ablation of the upper polyimide layer in the desired areas. Finally, the completed components are removed from their supporting substrate.

Polyimide, also known as PI, has been mass-produced since 1955. It is used in bearing materials, thrust washers, and semiconductor wafer clamps. It has high impact and dielectric strength, high heat resistance and a low coefficient of thermal expansion, and excellent mechanical, thermal, and electrical properties. Polyimide is typically applied in liquid form, and then thermally cured into a film or layer with the desired properties. The film can be patterned using photographic or other processes. Microelectronic applications include stress buffer, passivation layer, chip bonding, and interlayer dielectric.

Eugene de Juan Jr. et al. at Duke University Eye Center inserted retinal tacks into retinas in an effort to reattach retinas that had detached from the underlying choroid, which is the source of blood supply for the outer retina and thus the photoreceptors. See for example E. de Juan Jr., et al., "Retinal tacks", Am J Ophthalmol. 1985 Mar. 15; 99 (3):272-4.

Hansjoerg Beutel et al. at the Fraunhofer Institute for Biomedical Engineering IBMT demonstrated the bonding of a gold ball by force, temperature, and ultrasound onto an aluminum metal layer. See for example Hansjoerg Beutel, Thomas Stieglitz, Joerg-Uwe Meyer: "Versatile Microflex-Based Interconnection Technique," Proc. SPIE Conf. on Smart Electronics and MEMS, San Diego, Calif., March 1998, vol. 3328, pp 174-182. A robust bond can be achieved in this way. However, encapsulation proves difficult to effectively implement with this method. Gold, while biocompatible, is not completely stable under the conditions present in an implant device since it dissolves by electromigration when implanted in living tissue and subject to an electric current. See for example Marcel Pourbaix: "Atlas of Electrochemical Equilibria in Aqueous Solutions", National Association of Corrosion Engineers, Houston, 1974, pp 399-405.

A system for retinal stimulation comprising polyimide-based electrodes being coated with platinum black are described by Andreas Schneider and Thomas Stieglitz. See for example Andreas Schneider, Thomas Stieglitz: "Implantable Flexible Electrodes for Functional Electrical Stimulation", Medical Device Technology, 2004.

A process for activating a base polyimide layer prior to applying a top polyimide layer is described by Balasubrahmanyan Ganesh, who suggests to clean, roughen, and oxygenate the base polyimide by using reactive ion etching (RIE) in oxygen plasma for 10 s at 50 W, and 800 mTorr pressure in an Oxford Plasmalab-80 Plus system. The top polyimide layer is then spun-on immediately after the plasma roughening and the wafer is set aside for 45 min. See for example Balasubrahmanyan Ganesh: "A Polyimide Ribbon Cable for Neural Recording and Stimulation Systems", a Thesis for the Degree of Master of Science, Department of Materials Science and Engineering, The University of Utah, March 1998.

A process for activating a base polyimide layer prior to applying a top polyimide layer is described by Nancy Stoffel, Crystal Zhang and Edward J. Kramer. Stoffel et al. suggest using wet chemical treatments to hydrolyze the films according to a method reported by K. W. Lee et al. (1990). Stoffel et al. found solutions of both 1 M KOH and 1M tetramethyl ammonium hydroxide to be effective for polyimide films. Solutions of 0.2 M HCl and acetic acid were used and found to be effective for converting polyamate salt into a polyamic acid. See for example Nancy Stoffel, Crystal Zhang and Edward J. Kramer: "Adhesion of Polyimide Laminates", Application of Fracture Mechanics in Electronic Packaging and Materials, ASME, EEP-Vol. 11/MD-Vol. 64, pp. 79-84, 1995.

BRIEF SUMMARY OF THE INVENTION

The flexible circuit electrode array is electrically coupled by a flexible circuit cable, which pierces the sclera and is electrically coupled to an electronics package. The flexible circuit electrode array and the flexible circuit cable are formed of a single body.

The pressure applied against the retina, or other neural tissue, by an electrode array is critical. Low pressure causes increased electrical resistance between the array and retina, along with electrical field dispersion. High pressure may block blood flow within the retina causing a condition similar to glaucoma. Common flexible circuit fabrication techniques such as photolithography generally require that a flexible circuit electrode array be made flat. Since the retina is spherical, a flat array will necessarily apply more pressure near its edges, than at its center. The edges of a flexible circuit polymer array may be quite sharp and cut the delicate retinal tissue. Most polymers can be curved when heated in a mold. By applying the right amount of heat to a completed array, a curve can be induced matching the curve of the retina. With a thermoplastic polymer such as liquid crystal polymer, it may be further advantageous to repeatedly heat the flexible circuit in multiple molds, each with a decreasing radius.

The present invention provides a flexible circuit electrode array, comprising:
a) an insulating polymer layer;
b) at least one wire trace containing a base thin coating layer, an electrode layer and a top thin coating layer;
c) at least one electrode connected to the electrode layer of the wire trace through a via through the insulating polymer layer and the top thin coating layer.

The present invention further provides a method of manufacturing a flexible circuit electrode array, comprising:
a) depositing a metal trace layer containing a base coating layer, a conducting layer and a top coating layer on the insulator polymer base layer;
b) applying a layer of photoresist on the metal trace layer and patterning the metal trace layer and forming metal traces on the insulator polymer base layer;
c) activating the insulator polymer base layer and depositing a top insulator polymer layer forming one single insulating polymer layer with the base insulator polymer layer,
d) applying a thin metal layer and a layer of photoresist on the insulator polymer layer and patterning the insulator layer and the top coating layer to obtain at least one via; and
e) filling the via with electrode material.

The present invention provides a flexible circuit electrode array with the excellent adhesion and insulating properties of a polymer insulator reached by a new technique of activation of a base polymer layer prior to applying a top polymer layer wherein both polymer layers result in one polymer layer. The adhesion and insulating properties are further improved by applying a top metal layer on the electrode layer as an adhesion aid to the polymer.

The method of the present invention solves the long term problem of week adhesion between the insulator polymer base layer and the top insulator polymer layer. The method of the present invention provides an excellent adhesion between the polymer base layer and the polymer top layer and an excellent insulation of the trace metal.

DETAILED DESCRIPTION OF THE INVENTION

Figure 1:
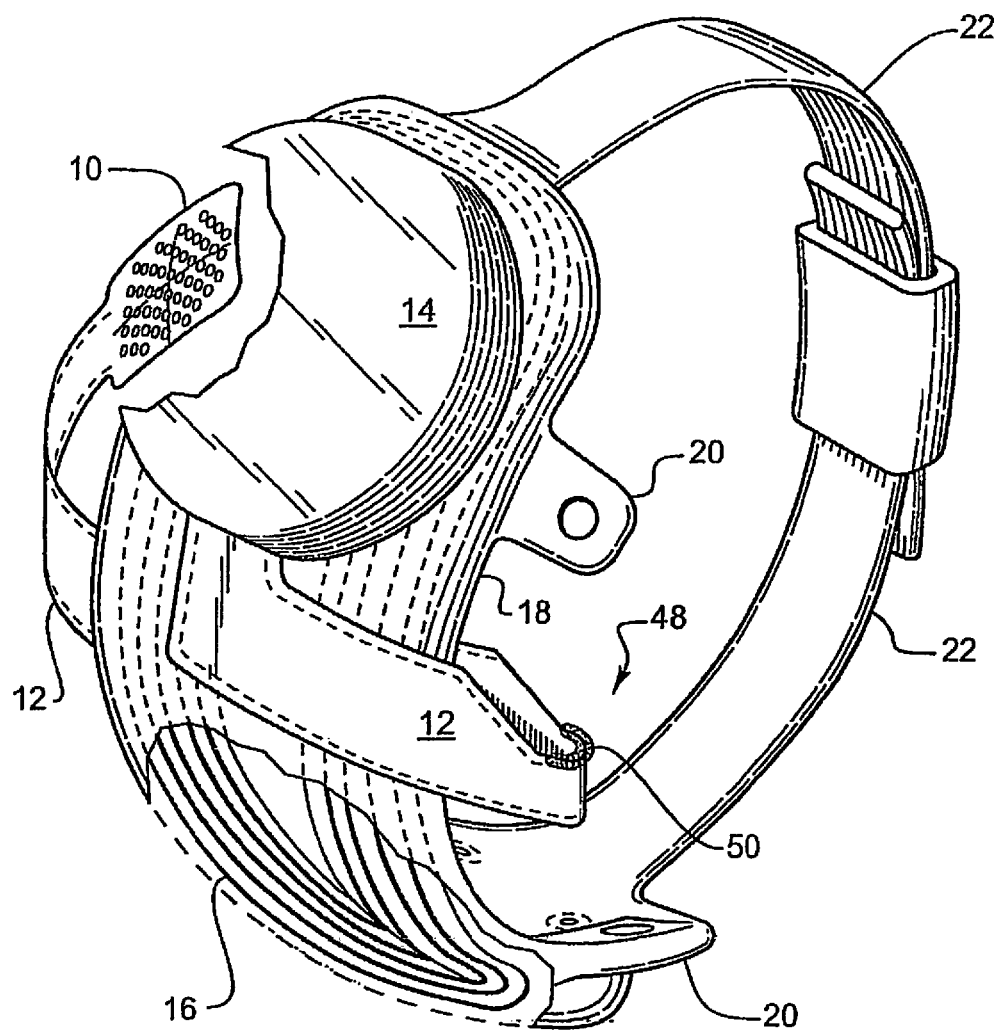
FIG. 1 depicts a perspective view of the implanted portion of the preferred retinal prosthesis including a twist in the array to reduce the width of a sclerotomy and a sleeve to promote sealing of the sclerotomy.

FIG. 1 shows a perspective view of the implanted portion of the preferred retinal prosthesis. A flexible circuit electrode array 10 is mounted by a retinal tack or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably, the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature 40 of a typical sclera. However, silicone remains flexible enough to accommodate implantation and to adapt to variations in the curvature 40 of an individual sclera. The secondary inductive coil 16 and molded body 18 are preferably oval shaped. A strap 22 can better support an oval shaped coil 16.

The implanted portion of the retinal prosthesis may include the additional feature of a gentle twist or fold 48 in the flexible circuit cable 12, where the flexible circuit cable 12 passes through the sclera (scleratomy). The twist 48 may be a simple sharp twist, or fold; or it may be a longer twist, forming a tube. While the tube is rounder, it reduces the flexibility of the flexible circuit cable 12. A simple fold reduces the width of the flexible circuit cable 12 with only minimal impact on flexibility.

Further, silicone or other pliable substance may be used to fill the center of the tube or fold 48 formed by the twisted flexible circuit cable 12. Further it is advantageous to provide a sleeve or coating 50 that promotes healing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating 50 of polyester, collagen, silicone, Gore-Tex® or similar material would bond with scleral tissue and promote healing. In particular, a porous material will allow scleral tissue to grow into the pores promoting a good bond.

The entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package 14 in an area of fatty tissue between the rectus muscles, eye motion does not cause any flexing which might fatigue, and eventually damage, the device.

Human vision provides a field of view that is wider than it is high. This is partially due to fact that we have two eyes, but even a single eye provides a field of view that is approximately 90° high and 140° to 160° degrees wide. It is, therefore, advantageous to provide a flexible circuit electrode array 10 that is wider than it is tall. This is equally applicable to a cortical visual array. In which case, the wider dimension is not horizontal on the visual cortex, but corresponds to horizontal in the visual scene.

Figure 2:
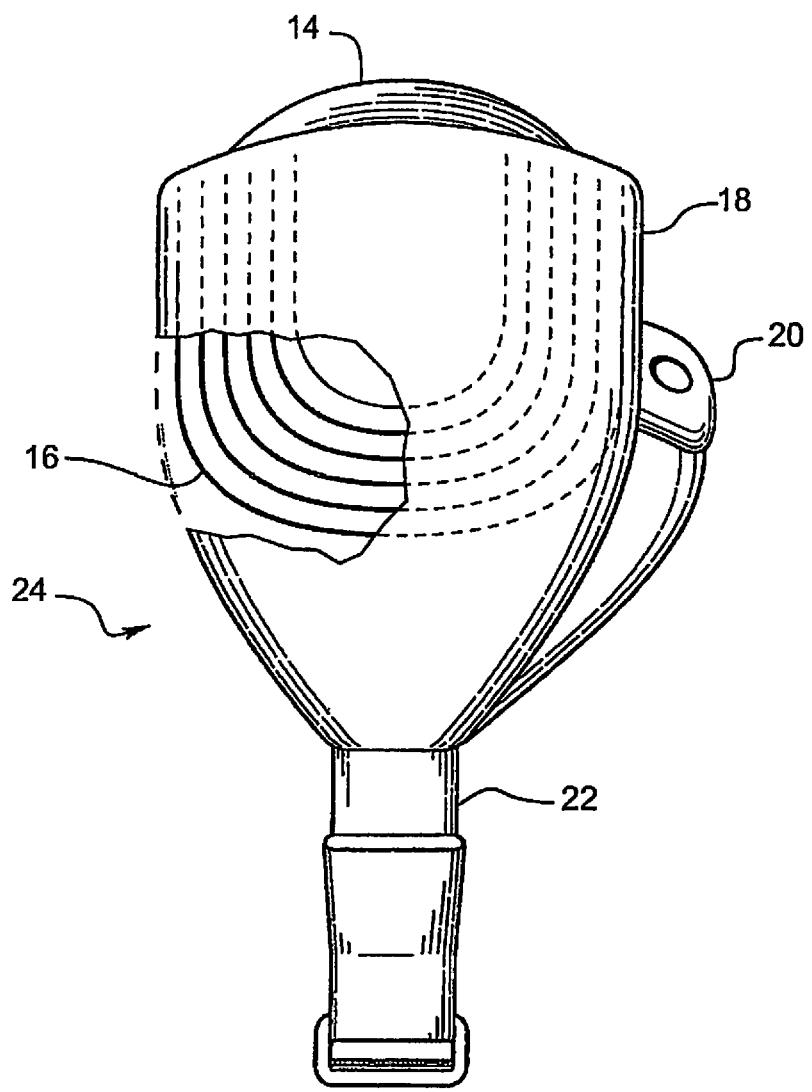
FIG. 2 depicts a perspective view of the implanted portion of the retinal prosthesis showing the fan tail in more detail.
Figure 3A:
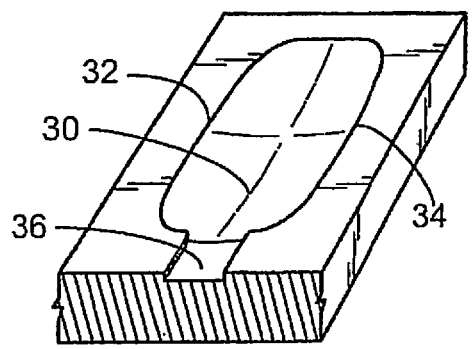
FIGS. 3a-3e depict a perspective view of molds for forming the flexible circuit array in a curve.
Figure 3B:
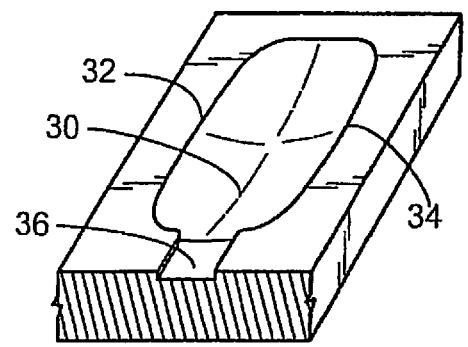
Figure 3C:
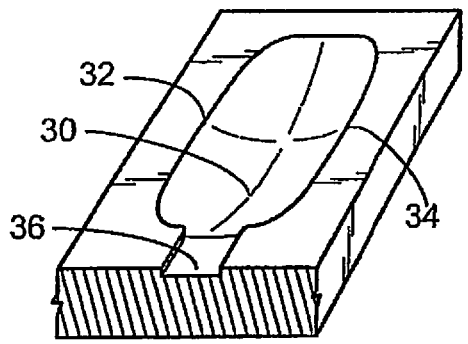
Figure 3D:
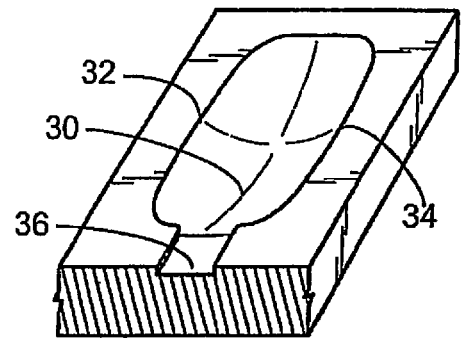
Figure 3E:
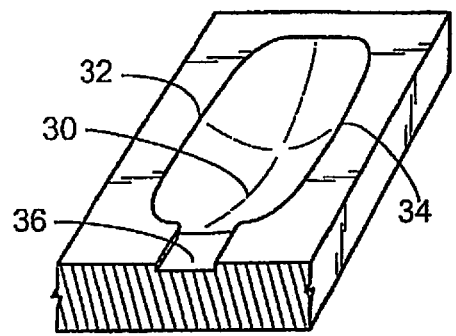

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit electrode array 10 is a made by the following process. First, a layer of polymer is applied to a supporting substrate (not part of the array) such as glass. The polymer layer or films of the present invention can be made, for example, from any one of the various polyfluorocarbons, polyethylene, polypropylene, polyimide, polyamide, silicone or other biologically inert organic polymers. Layers may be applied by spinning, meniscus coating, casting, sputtering or other physical or chemical vapor deposition, or similar process. Subsequently, a metal layer is applied to the polymer. The metal is patterned by photolithographic process. Preferably, a photoresist is applied and patterned by photolithography followed by a wet etch of the unprotected metal. Alternatively, the metal can be patterned by lift-off technique, laser ablation or direct write techniques.

It is advantageous to make the metal thicker at the electrode and bond pad to improve electrical continuity. This can be accomplished through any of the above methods or by electroplating. Then the top layer of polymer is applied over the metal. Openings in the top layer for electrical contact to the electronics package 14 and the flexible circuit electrode array 10 may be accomplished by laser ablation or reactive ion etching (RIE) or photolithograph and wet etch. Making the electrode openings in the top layer smaller than the electrodes promotes adhesion by avoiding delaminating around the electrode edges.

The pressure applied against the retina by the flexible circuit electrode array 10 is critical. Too little pressure causes increased electrical resistance between the array and retina. Common flexible circuit fabrication techniques such as photolithography generally require that a flexible circuit electrode array 10 be made flat. Since the retina is spherical, a flat array will necessarily apply more pressure near its edges than at its center. With most polymers, it is possible to curve them when heated in a mold. By applying the right amount of heat to a completed array, a curve can be induced that matches the curve of the retina. To minimize warping, it is often advantageous to repeatedly heat the flexible circuit in multiple molds, each with a decreasing radius. FIG. 3 illustrates a series of molds according to the preferred embodiment. Since the flexible circuit will maintain a constant length, the curvature 30 must be slowly increased along that length. As the curvature 30 decreases in successive molds (FIGS. 3*a*-3*e*) the straight line length between ends 32 and 34, must decrease to keep the length along the curvature 30 constant, where mold 3E approximates the curvature 30 of the retina or other desired neural tissue. The molds provide a further opening 36 for the flexible circuit cable 12 of the array to exit the mold without excessive curvature.

It should be noted that suitable polymers include thermoplastic materials and thermoset materials. While a thermoplastic material will provide some stretch when heated a thermoset material will not. The successive molds are, therefore, advantageous only with a thermoplastic material. A thermoset material works as well in a single mold as it will with successive smaller molds. It should be noted that, particularly with a thermoset material, excessive curvature 30 in three dimensions will cause the polymer material to wrinkle at the edges. This can cause damage to both the array and the retina. Hence, the amount of curvature 30 is a compromise between the desired curvature, array surface area, and the properties of the material.

Figure 4:
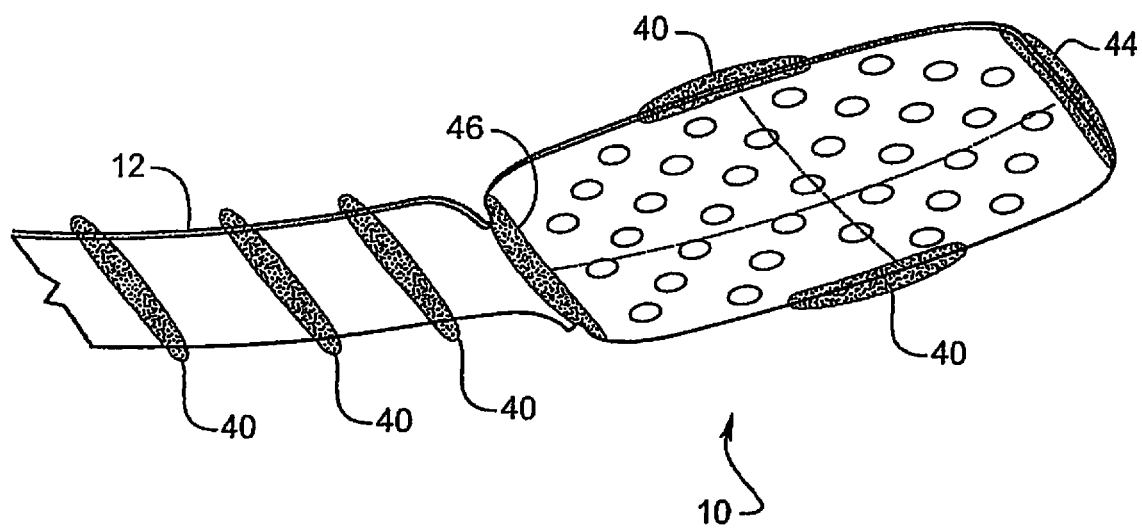
FIG. 4 depicts an alternative view of the invention with ribs to help maintain curvature and prevent retinal damage.

Referring to FIG. 4, the edges of the polymer layers are often sharp. There is a risk that the sharp edges of a flexible circuit will cut into delicate retinal tissue. It is advantageous to add a soft material, such as silicone, to the edges of a flexible circuit electrode array 10 to round the edges and protect the retina. Silicone around the entire edge may make the flexible circuit less flexible. It is advantageous to provide silicone bumpers or ribs to hold the edge of the flexible circuit electrode array 10 away from the retinal tissue. Curvature 40 fits against the retina. The leading edge 44 is most likely to cause damage and is therefore fit with molded silicone bumper. Also, edge 46, where the array lifts off the retina, can cause damage and should be fit with a bumper. Any space along the side edges of curvature 40 may cause damage and may be fit with bumpers as well. It is also possible for the flexible circuit cable 12 of the electrode array to contact the retina. It is, therefore, advantageous to add periodic bumpers along the cable 12.

It is also advantageous to create a reverse curve or service loop in the flexible circuit cable 12 of the flexible circuit electrode array 10 to gently lift the flexible circuit cable 12 off the retina and curve it away from the retina, before it pierces the sclera at a sclerotomy. It is not necessary to heat curve the service loop as described above, the flexible circuit electrode array 10 can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array 10 must be inside the sclera in order to contact the retina. The sclera must be cut through at the pars plana, forming a sclerotomy, and the flexible circuit passed through the sclerotomy. A flexible circuit is thin but wide. The more electrode wires, the wider the flexible circuit must be. It is difficult to seal a sclerotomy over a flexible circuit wide enough to support enough wires for a high resolution array.

Figure 5:
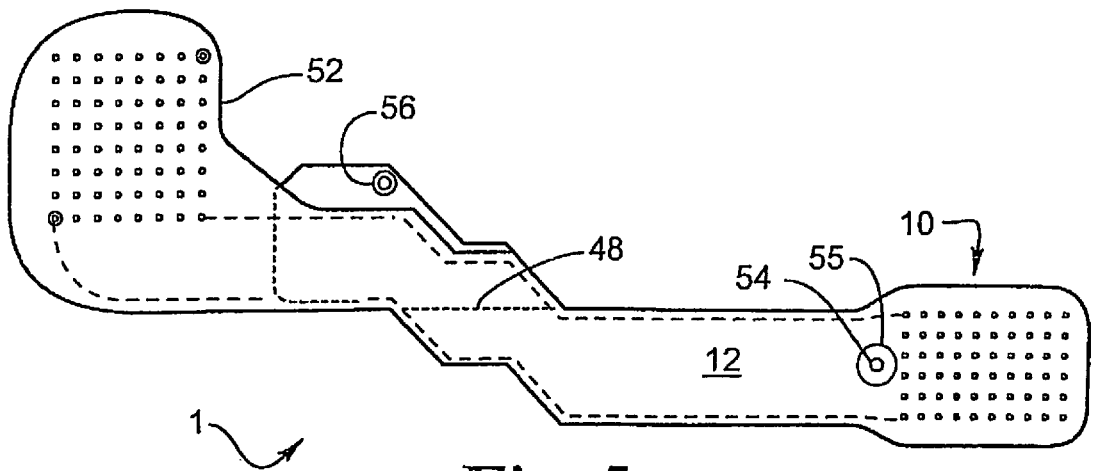
FIG. 5 depicts a top view of a body comprising a flexible circuit electrode array, a flexible circuit cable and a bond pad before it is folded and attached to the implanted portion.

FIG. 5 shows a body 1 containing the flexible circuit electrode array 10, the flexible circuit cable 12 and the interconnection pad 52 prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, an attachment point 54 is provided near the flexible circuit electrode array 10. A retina tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

Figure 6:
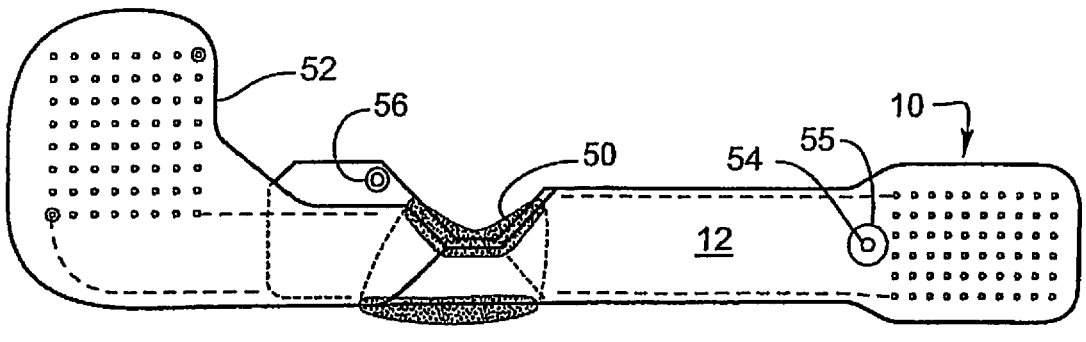
FIG. 6 depicts a top view of a body comprising a flexible circuit electrode array, a flexible circuit cable and a bond pad after it is folded.
Figure 7:
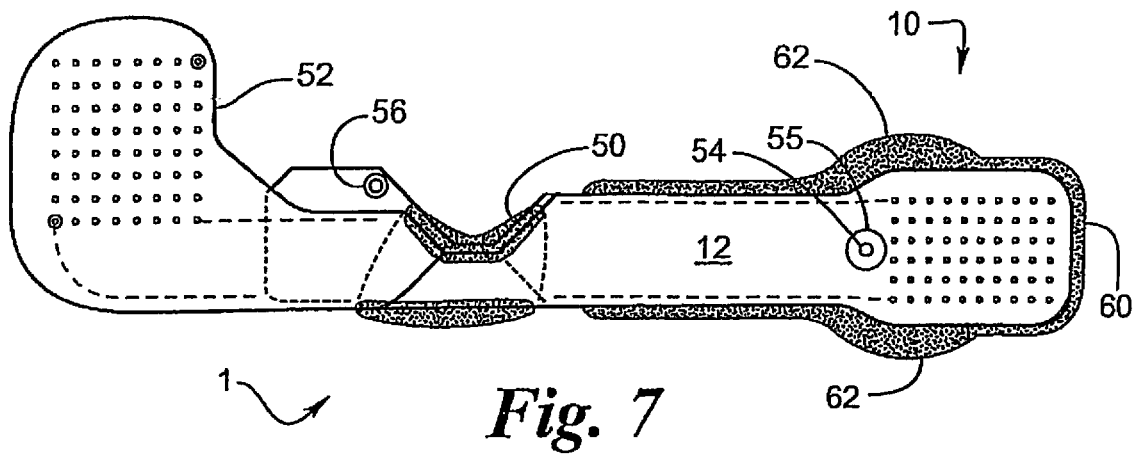
FIG. 7 depicts a top view of a body comprising a flexible circuit electrode array, a flexible circuit cable and a bond pad after it is folded, with a protective skirt.

FIG. 6 shows the flexible circuit electrode array 10 after the flexible circuit cable 12 is folded at the fold 48 to form a narrowed section. The flexible circuit cable 12 may include a twist or tube shape as well. With a retinal prosthesis as shown in FIG. 1, the interconnection pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package 14 to prevent any movement in the electronics package 14 from being transmitted to the flexible circuit electrode array 10.

Alternatively, a segment of the flexible circuit cable 12 can be reinforced to permit it to be secured directly with a suture.

An alternative to the bumpers described in FIG. 4, is a skirt of silicone or other pliable material as shown in FIGS. 7 to 10. A skirt 60 covers the flexible circuit electrode array 10, and extends beyond its edges. It is further advantageous to include windows 62 adjacent to the attachment point 54 to spread any stress of attachment over a larger area of the retina. There are several ways of forming and bonding the skirt 60. The skirt 60 may be directly bonded through surface activation or indirectly bonded using an adhesive.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such a polyimide may be used for the bottom layer and a relatively softer polymer such a silicone may be used for the top layer including an integral skirt to protect delicate neural tissue.

Figure 8:
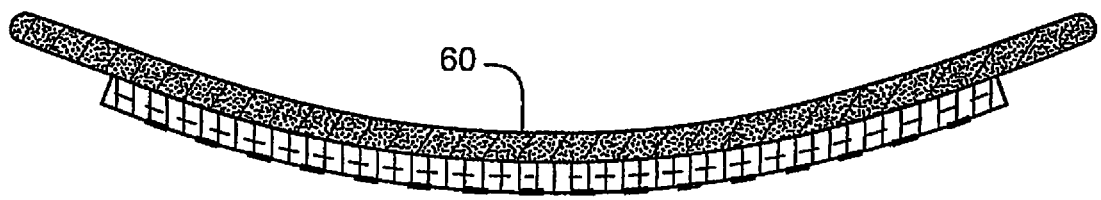
FIG. 8 depicts a cross-sectional view of a flexible circuit array with a protective skirt bonded to the back side of the flexible circuit array.
Figure 9:
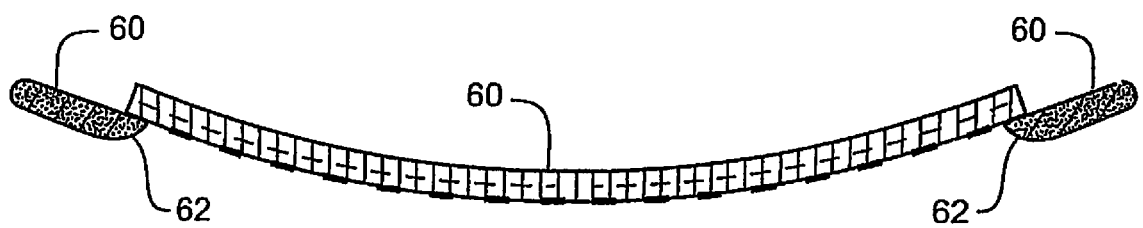
FIG. 9 depicts a cross-sectional view of a flexible circuit array with a protective skirt bonded to the front side of the flexible circuit array.

The simplest solution is to bond the skirt 60 to the back side away from the retina of the flexible circuit electrode array 10 as shown in FIG. 8. While this is the simplest mechanical solution, sharp edges of the flexible circuit electrode array 10 may contact the delicate retina tissue. Bonding the skirt to the front side toward the retina of the flexible circuit electrode array 10, as shown in FIG. 9, will protect the retina from sharp edges of the flexible circuit electrode array 10. However, a window 62 must be cut in the skirt 60 around the electrodes. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

Figure 10:
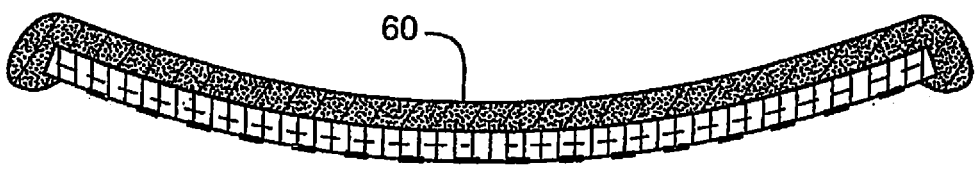
FIG. 10 depicts a cross-sectional view of a flexible circuit array with a protective skirt bonded to the back side of the flexible circuit array and molded around the edges of the flexible circuit array.

FIG. 10 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side, of the flexible circuit electrode array 10, the portion extending beyond the front side of the flexible circuit electrode array 10 can be much smaller. This limits any additional spacing between the electrodes and the retinal tissue.

Figure 11:
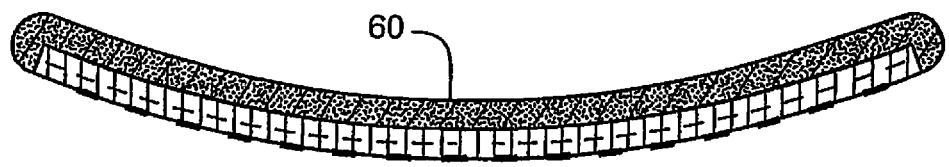
FIG. 11 depicts a cross-sectional view of a flexible circuit array with a protective skirt bonded to the back side of the flexible circuit array and molded around the edges of the flexible circuit array and flush with the front side of the array.

FIG. 11 shows a flexible circuit electrode array 10 similar to FIG. 10, with the skirt 60 flush with the front side of the flexible circuit electrode array 10 rather than extending beyond the front side. While this is more difficult to manufacture, it does not lift the electrodes off the retinal surface as with the array in FIG. 10. It should be noted that FIGS. 8, 10, and 11 show skirt 60 material along the back of the flexible circuit electrode array 10 that is not necessary other than for bonding purposes. If there is sufficient bond with the flexible circuit electrode array 10, it may be advantageous to thin or remove portions of the skirt 60 material for weight reduction.

The electrode of the present invention preferably contains platinum. Platinum can be present in any form in the electrode. The electrode has preferably increased surface area for greater ability to transfer charge and also having sufficient physical and structural strength to withstand physical stress encountered in its intended use. The electrode contains platinum having a fractal configuration so called platinum gray with an increase in surface area of at least 5 times when compared to shiny platinum of the same geometry and also having improved resistance to physical stress when compared to platinum black. Platinum gray is described in US 2003/0192784 "Platinum Electrode and Method for Manufacturing the Same" to David Zhou, the disclosure of which is incorporated herein by reference. The electrodes of the preferred embodiment are too small to display a color without significant magnification. The process of electroplating the surface coating of platinum gray comprising plating at a moderate rate, i.e., at a rate that is faster than the rate necessary to produce shiny platinum and that is less than the rate necessary to produce platinum black.

The flexible circuit electrode array 10 is manufactured in layers. A base layer of polymer is laid down, commonly by some form of chemical vapor deposition, spinning, meniscus coating or casting on a supporting rigid substrate like glass. A layer of metal (preferably platinum), preferably sandwiched by layers of another metal, for example, titanium, is applied to the polymer base layer and patterned to create electrodes and traces for those electrodes. Patterning is commonly done by photolithographic methods. The electrodes may be built up by electroplating or similar method to increase the surface area of the electrode and to allow for some reduction in the electrode over time. Similar plating may also be applied to the bond pads. See FIGS. 5 to 7. A top polymer layer is applied over the metal layer and patterned to leave openings for the electrodes, or openings are created later by means such as laser ablation. It is advantageous to allow an overlap of the top polymer layer over the electrodes to promote better adhesion between the layers, and to avoid increased electrode reduction along their edges. Alternatively, multiple alternating layers of metal and polymer may be applied to obtain more metal traces within a given width.

Figure 12:
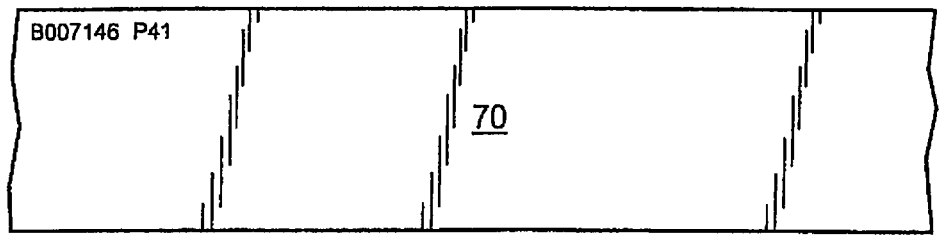
FIG. 12 depicts a top view on a supporting glass plate substrate which is marked with a batch and plate identification code.

FIG. 12 depicts a supporting rigid substrate 70 which may be marked with a batch and plate identification code by mechanical engraving. The supporting substrate 70 is a rigid material like glass.

Figure 13:
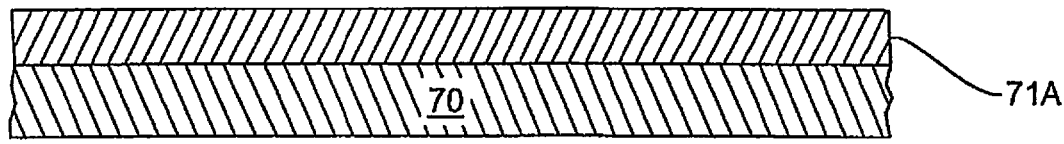
FIG. 13 depicts a cross-sectional view of a layer of polyimide which is applied onto the front side of the glass plate and cured.

FIG. 13 shows a polymer layer 71a which is applied onto the front side of the supporting substrate 70. The polymer can contain polyfluorocarbons, polyethylene, polypropylene, silicone, polyamide, polyimide, liquid crystal polymer (LCP), poly-para-xylylene (GALXYL® Parylene), polyaryletherketone (Peek®) or other similar polymers. The preferred polymer according to the present invention is polyimide. Polyimide is biocompatible and shows excellent properties as insulator for the trace metal and electrodes in the electrode array. Polyimide is preferably obtained by imidization of polyamic acid. Polyamic acid is a precursor of the polyimide. By heating the polyamic acid to a temperature of preferably 100° C. to 400° C. the imidization of the polyamic acid is conducted. The following formula shows an example of imidization of polyamic acid to polyimide.

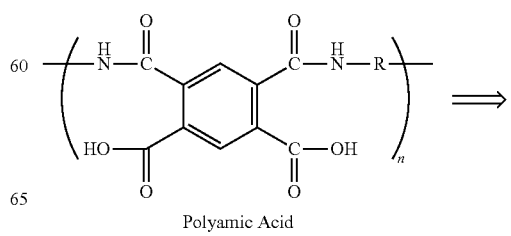

Polyamic Acid

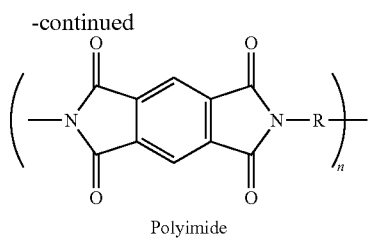

Polyimide

R is a bivalent organic group, like 4,4' oxydianiline or p-phenylendiamine and n is an integer >1. Two polyimides are preferably used within the present invention. PMDA/ODA (derived from polymellitic dianhydride (PMDA) and 4,4' oxydianiline (ODA)) and BPDA/PDA (derived from 3,3',4,4'-biphenyltetracarboxylic dianhydride (BPDA) and p-phenylendiamine (PDA)). The polyimide layer 71a is preferably obtained according to the present invention with a thickness of the liquid precursor of 1.0 μm to 10 μm, preferably 4.0 μm to 7.0 μm, and most preferably 5.0 μm to 6.0 μm. The plate is placed in a plasma cleaner. An adhesion promoter is applied on the plate and dried by letting the plate sit for at least 5 min. Spin speed of a spinner and ramp up time, spin time, and ramp down time are adjusted and polyamic acid is applied. The plate is soft baked on a hotplate at 90° C. to 110° C. whereby the solvents in the polyimide are evaporated. Then the polyimide is cured in a high temperature nitrogen purged oven.

Figure 14:
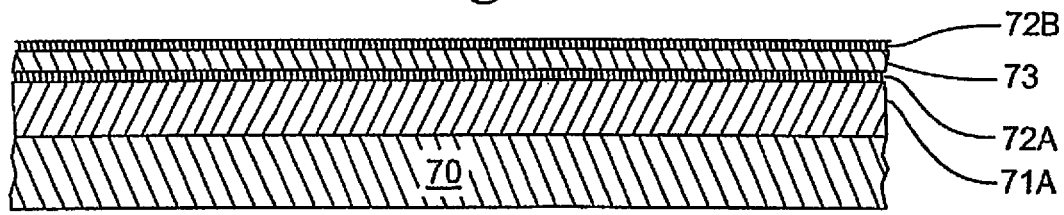
FIG. 14 depicts a cross-sectional view of layer deposition of titanium/platinum/titanium thin film stack from which conductor traces are patterned.

FIG. 14 shows that a first thin metal layer 72a containing titanium, chromium, tantalum or an alloy thereof or a combination of two or more alloys or metal layers thereof, having a thickness of 0.01 μm to 0.1 μm, preferably 0.03 μm to 0.07 μm, and most preferably 0.04 μm to 0.06 μm is applied on the base polymer layer 71a preferably by magnetron sputtering. A layer of electrode 73, containing platinum, tantalum, iridium, palladium, rhodium, rhenium, or alloys thereof or a combination of two or more alloys or metal layers thereof, having a thickness of 0.1 μm to 1.0 μm, preferably 0.3 μm to 0.7 μm, and most preferably 0.4 μm to 0.6 μm is applied on the thin metal layer 72a preferably by magnetron sputtering. A top thin layer of metal 72b, having a thickness of 0.05 μm to 0.15 μm, preferably 0.08 μm to 0.13 μm, and most preferably 0.08 μm to 0.12 μm, which preferably contains titanium, chromium, tantalum or an alloy thereof or a combination of two or more alloys or metal layers thereof, and particularly the same as the metal layer 72a, is applied onto the layer of platinum 73 preferably by magnetron sputtering yielding a thin film stack.

The trace metal of the present invention most preferably contains a lower layer of 0.04 μm to 0.06 μm thick titanium film 72a, a 0.4 μm to 0.6 μm thick platinum layer 73 and a 0.08 μm 0.12 μm thin top titanium film 72b. The present invention provides trace metal with a thin top titanium film 72b. The top titanium film 72b performs an expected strong adhesion with the upper polyimide layer 71b, which is applied as a precursor and is subsequently cured to polyimide. The state of the art teaches to omit a top layer of titanium on top of the platinum layer, because partial oxidation of the titanium surface would weaken the adhesion to polyimide. The present invention has shown a strong and unexpected adhesion a top titanium layer 72b to polyimide 71 despite the contrary prior art teaching.

Figure 15:
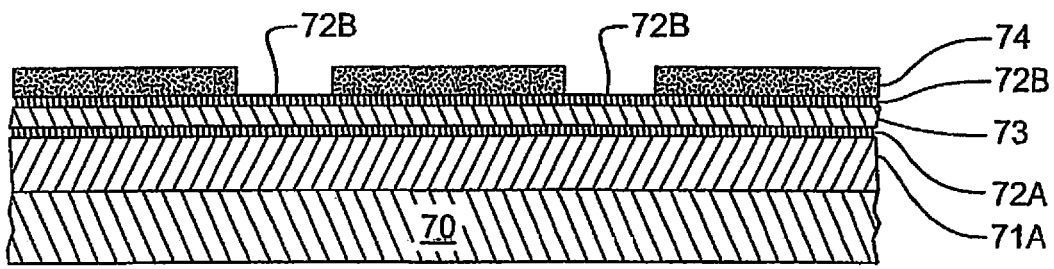
FIG. 15 depicts a cross-sectional view of photoresist layer deposition on the titanium/platinum/titanium thin film stack after the photoresist layer is exposed to irradiation through a mask and the radiated areas of the photoresist layer are removed during photolithographic processing to selectively mask titanium/platinum/titanium thin film stack in areas where conductor traces are to remain.

FIG. 15 shows a positive photoresist 74 which is applied on the metal titanium layer 72b. The photoresist layer 74 is irradiated by UV light through a mask whereby a pattern is obtained. The irradiated areas of the photoresist layer 74 are removed. The removed areas of the photoresist layer 74 masked selectively the areas where vias and traces are obtained. In this process the plate front side is first dehydrated. A mask aligner is turned on prior to use. The spin speed of a spinner is adjusted to 1700 rpm to 1900 rpm. The ramp up time, spin time, and ramp down time are adjusted to 3 s to 7 s, 15 s to 25 s, and 3 s to 7 s. Positive photoresist is poured onto the center of the plate to form a puddle that is 5.8 cm to 6.6 cm in diameter. The plate is soft baked on a hot plate at 100° C. to 110° C. for 25 s to 35 s. The required exposure dose is 80 mJ/cm²±5 mJ/cm² at 436 nm. The plate is aligned under a mask pattern in the mask aligner. The plate is exposed in the mask aligner. The plate is developed in developer for 40 s to 50 s (seconds) with manual agitation of a carrier boat. The exposed photoresist is dissolved during the development. Then the plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen.

Figure 16:
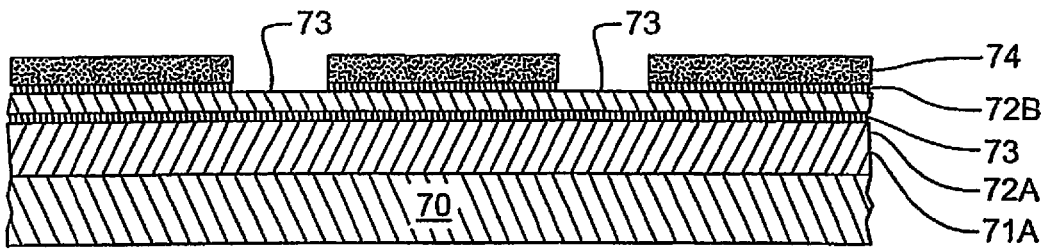
FIG. 16 depicts a cross-sectional view of the layer structure after the removal of the top layer from titanium/platinum/titanium trace metal stack in areas exposed during photolithography.

FIG. 16 shows how the thin top layer 72b is removed in the exposed areas. Typically the preferred titanium is removed at 20° C. to 30° C. for 50 s to 70 s with dilute hydrofluoric acid in a container. The plate is loaded into a carrier boat before etching the titanium. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only.

Figure 17:
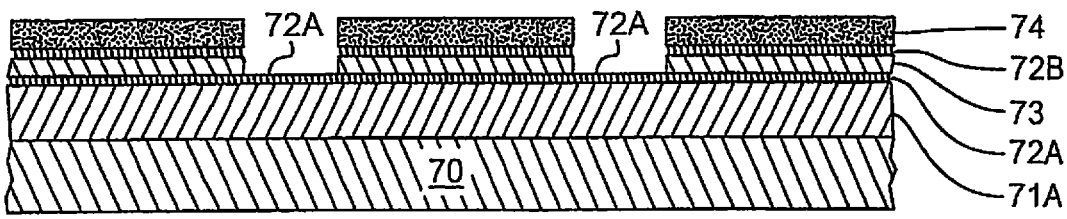
FIG. 17 depicts a cross-sectional view of the layer structure after the removal of the middle layer from titanium/platinum/titanium trace metal stack in areas exposed during photolithography.

FIG. 17 shows platinum being removed from the layer 73 by wet etch in the exposed areas. The plate is loaded into a carrier boat for removing platinum. Typically the preferred platinum is removed with Aqua Regia, which is a mixture of hydrochloric acid and nitric acid and water, at 60° C. to 70° C. for 7 min to 8 min to 10 min with continuous automatic agitation by 5 cm stir bar rotating at 400 rpm to 600 rpm. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only.

Figure 18:
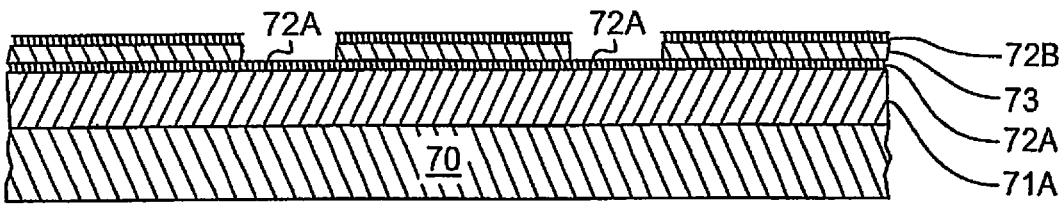
FIG. 18 depicts a cross-sectional view of the layer structure after the removal of residual photoresist from the trace metal surface.

FIG. 18 shows the residual photoresist layer 74 being removed with a liquid immersion solvent. The plate is soaked in acetone for 1 min to 3 min with manual agitation of the carrier boat at least every 15 s to 25 s. Then the plate is soaked in isopropanol for 1 min to 3 min with manual agitation of the carrier boat at least every 15 s to 25 s.

Figure 19:
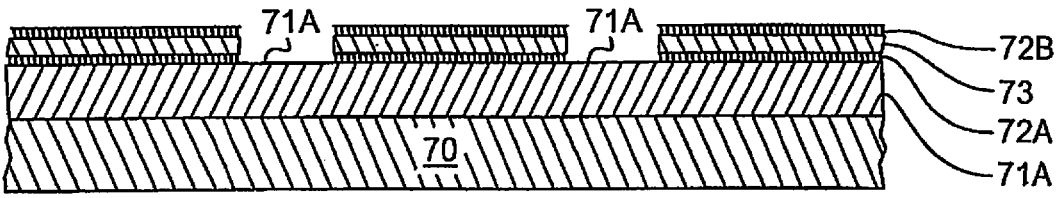
FIG. 19 depicts a cross-sectional view of the layer structure after the removal of bottom layer from titanium/platinum/titanium trace metal stack in areas exposed during photolithography and preceding etches.

FIG. 19 shows that metal is removed from the thin titanium layer 72a by wet etch in the masked areas. Typically the preferred titanium is removed at 20° C. to 30° C. for 30 s to 40 s with dilute hydrofluoric acid. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only. The plate is then dehydrated in preheated oven at 110° C. to 130° C. for 8 min to 10 min.

Figure 20:
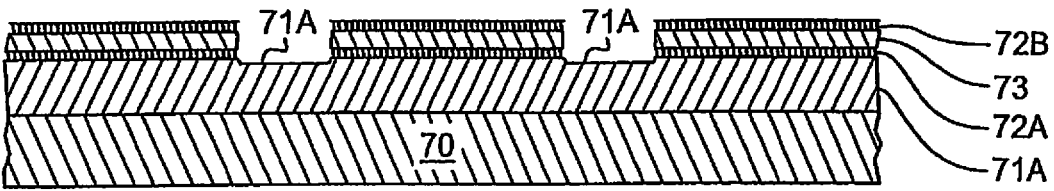
FIG. 20 depicts a cross-sectional view of the layer structure after activating and roughening and partial removal of base polyimide surface layer in all areas not covered by trace metal conductors.

FIG. 20 shows that the areas where titanium 72a and 72b and platinum 73 were removed are not covered by trace metal conductors but are open and base polyimide 71a is the surface layer. Base polyimide surface layer 71a is then activated by RIE in all areas not covered by trace metal conductors. The plate is loaded in this process into a plasma cleaner. The plate is cleaned in 400 mTorr to 600 mTorr $O_2$ for 4 min to 6 min at 180 W to 220 W (W stands for Watt). Then the plate is treated in KOH-deimidization bath at 20° C. to 30° C. for 4 min to 6 min with manual agitation of the carrier boat at least every 50 s to 70 s. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only. The plate is treated in an HCl-deimidization bath at 20° C. to 30° C. for 4 min to 6 min with manual agitation of the carrier boat at least every 50 s to 70 s. The plate is rinsed in the lower cascade rinse bath for 50 s to 70 s. The plate is rinsed in the middle cascade rinse bath for 50 s to 70 s. The plate is rinsed in the bubbler cascade rinse bath for 50 s to 70 s. The plate is dried with filtered nitrogen, front side only. The plate is soaked in isopropanol at 20° C. to 30° C. for 1 min to 2 min with manual agitation of the carrier boat at least every 15 s to 25 s. The plate is dried with filtered nitrogen, front side only. The plate is dehydrated under vacuum pressure of less than 100 mTorr for at least 2 hr.

The activation process according to the present invention provides a surface of the base layer 71*a* which is deimidized and therefore the surface is similar to the uncured state. The imidization process obtained during curing is now reversed.

The activated surface layer of the base polyimide layer is chemically very similar to the precursor of the top polyimide layer 71*b* which is applied to yield a top layer. When the precursor of the top layer 71*b* is applied on the activated and deimidized base layer 71*a* then there is no boundary between the two layers in the contact area.

Figure 21:
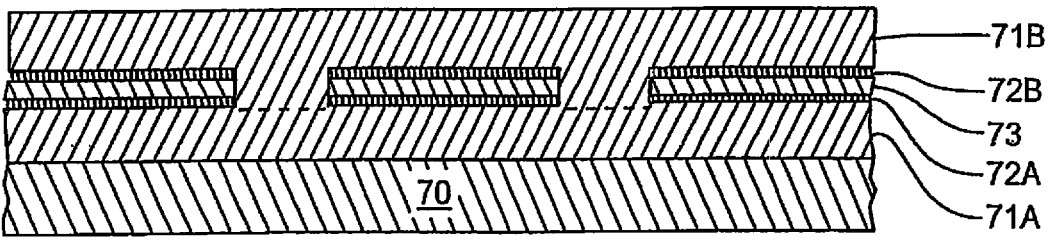
FIG. 21 depicts a cross-sectional view of the layer structure after a layer of polyimide is spun over the underlying structures and cured.

FIG. 21 shows how a top layer of polymer 71*b* is applied onto the top of base polymer layer 71*a*. The polymer contains polyfluorocarbons, polyethylene, polypropylene, silicone, polyamide, polyimide, liquid crystal polymer (LCP), poly-para-xylylene (GALXYL® Parylene), polyaryletherketone (Peek®) or other similar polymers. Polyimide shows excellent properties as an insulator for the trace metal and electrodes in the electrode array. Polyimide is preferably obtained by imidization of polyamic acid. Polyamic acid is a precursor of the polyimide. The imidization of the polyamic acid to polyimide is conducted by heating the polyamic acid at a temperature of preferably 100° C. to 400° C. The polyimide layer 71*b* is preferably obtained according to the present invention with a thickness of 1.0 µm to 10 µm, preferably 4.0 µm to 7.0 µm, and most preferably 5.0 µm to 6.0 µm. The plate is placed in this process in a plasma cleaner. An adhesion promoter is applied on the plate and dried off by letting the plate sit for at least 5 min. Spin speed of a spinner and ramp up time, spin time, and ramp down time are adjusted and polyamic acid is applied. The plate is soft baked on a hotplate at 100° C. to 110° C. whereby the solvents in the polyimide are evaporated. The polyimide is cured in a high temperature nitrogen purged oven.

Figure 22:
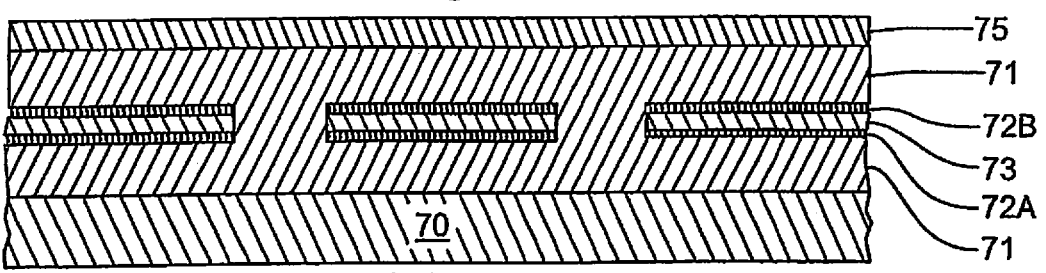
FIG. 22 depicts a cross-sectional view of the layer structure after curing the polyimide and after depositing an aluminum thin film layer on top of the polyimide layer that will serve to define openings in the top polyimide insulation.

FIG. 22 shows that base polyimide layer 71*a* and top polyimide layer 71*b* become one polyimide layer 71 performing a high adhesion to the trace metal. An insulation mask of aluminum thin film 75 is applied preferably by magnetron sputtering on top of the polyimide layer 71 having a thickness of 0.5 µm to 1.5 µm, preferably 0.7 µm to 1.3 µm, and most preferably 0.9 µm to 1.1 µm.

Figure 23:
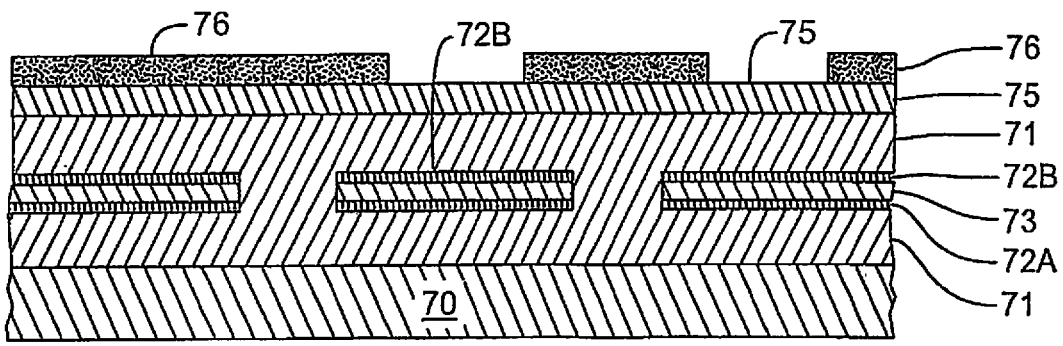
FIG. 23 depicts a cross-sectional view of the layer structure after a photoresist layer is deposited on the aluminum layer and exposed to irradiation through a mask and the radiated areas of the photoresist layer are removed during photolithographic processing to selectively mask aluminum thin film layer in areas that are to remain.

FIG. 23 shows that a positive photoresist 76 is applied on the aluminum layer 75. The photoresist layer 76 is irradiated by UV light through a mask whereby a pattern is obtained. The irradiated areas of the photoresist layer 76 are removed by a solvent. The removed areas of the photoresist layer 76 expose selectively the areas where vias are to be obtained in the further process. The plate front side is dehydrated at 110° C. to 130° C. for 15 min to 25 min. A mask aligner is turned on prior to use. The spin speed of a spinner is adjusted to 2800 rpm to 3200 rpm. The ramp up time, spin time, and ramp down time are adjusted to 15 s to 25 s, 1 s to 2 s, and 2 s to 4 s respectively. Positive photoresist 76 is poured onto the center of the plate to form a puddle that is 3.6 cm to 4.0 cm in diameter. The plate is soft baked on a hot plate at 110° C. to 120° C. for 4 min to 5 min. The required exposure dose is 470 mJ/cm$^2$ to 490 mJ/cm$^2$ at 436 nm. The Insulation Vias photomask is used in the aligner. The plate is aligned under mask pattern in the mask aligner. The plate is exposed in the mask aligner. The plate is developed in a developer for 40 s to 50 s with manual agitation of the carrier boat. The plate is developed in heated developer mixture at 20° C. to 30° C. for 4 min to 6 min with manual agitation every 30 s. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only. The plate is hard baked in oven for 25 min 35 min at 80° C. to 100° C.

Figure 24:
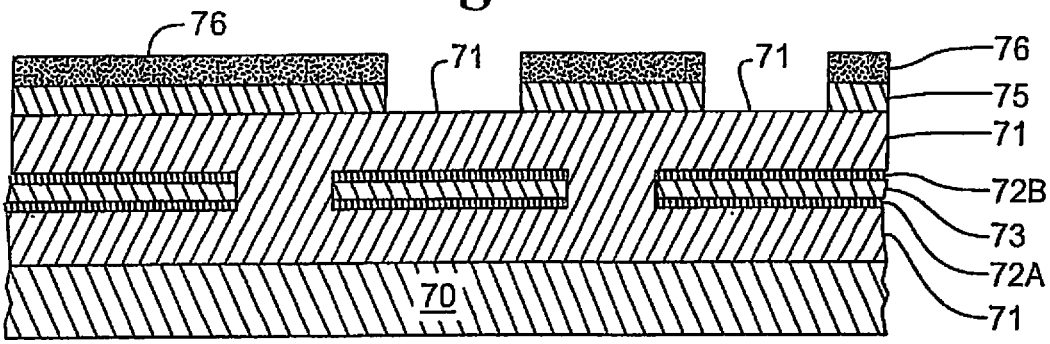
FIG. 24 depicts a cross-sectional view of the layer structure after the removal of aluminum layer in areas exposed during photolithography and preceding etches.

FIG. 24 shows that the aluminum layer 75 is removed in exposed areas by wet etch. The plate is plasma cleaned in this process in 500 mTorr to 600 mTorr O$_2$ for 4 min to 6 min at 180 W to 220 W. The plate is treated in heated Al Etch, containing 71% to 73% phosphoric acid, 9% to 11% acetic acid, and 1% to 3% nitric acid, at 30° C. to 40° C. for 9 min to 12 min with manual agitation every 50 s to 70 s. The plate is first rinsed in a lower cascade rinse bath for 1 min to 3 min then in a middle cascade rinse bath for 1 min to 3 min and finally in a bubbler cascade rinse bath for 1 min to 3 min. The plate is dried with filtered nitrogen, front side only. The plate is dehydrated for 25 min to 35 min at 90° C. to 110° C.

Figure 25:
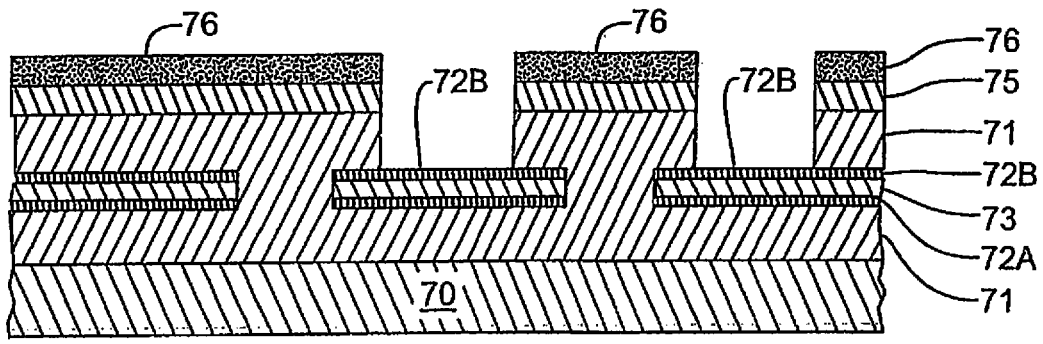
FIG. 25 depicts a cross-sectional view of the layer structure after the removal of top polyimide to create vias to trace metal in areas defined by aluminum etch mask.

FIG. 25 shows that polyimide surface layer 71 is removed by RIE (Reactive Ion Etching) in all areas not covered by the aluminum layer 75.

Figure 26:
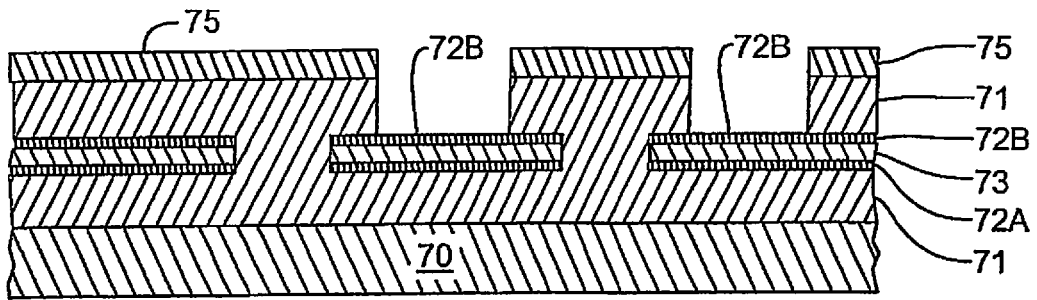
FIG. 26 depicts a cross-sectional view of the layer structure after the removal of the remaining photoresist from surface.

FIG. 26 shows that the residual photoresist layer 76 was removed from the aluminum layer 75 with a liquid immersion solvent. The plate is soaked in acetone for 1 min to 3 min with manual agitation of the carrier boat at least every 15 s to 25 s. Then the plate is soaked in isopropanol for 1 min to 3 min with manual agitation of the carrier boat at least every 15 s to 25 s. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only.

Figure 27:
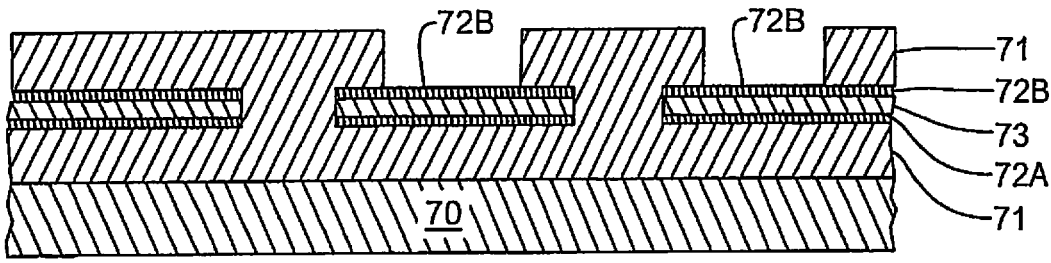
FIG. 27 depicts a cross-sectional view of the layer structure after the removal of remaining aluminum mask layer.

FIG. 27 shows that remaining insulation mask aluminum layer 75 is removed from the polyimide 71 layer by wet etch. The plate is plasma cleaned in 550 mTorr O$_2$ for 4 min to 6 min at 180 W to 220 W. The plate is treated in heated Al Etch at 30° C. to 40° C. for 9 min to 11 min with manual agitation every 50 s to 70 s. The plate is first rinsed in a lower cascade rinse bath for 1 min to 3 min then in a middle cascade rinse bath for 1 min to 3 min and finally in a bubbler cascade rinse bath for 1 min to 3 min. The plate is dried with filtered nitrogen, front side only. The plate is dehydrated for 25 min to 30 min at 100° C. to 110° C.

Figure 28:
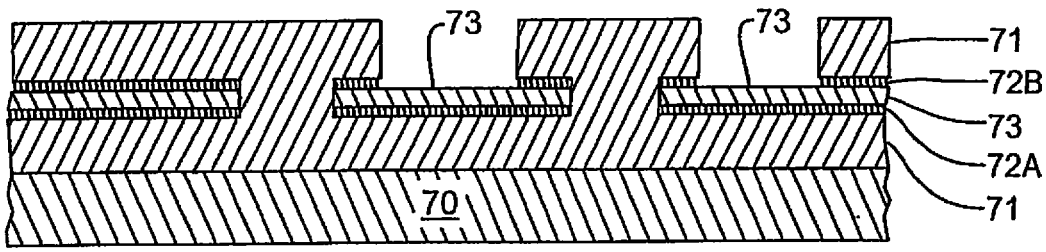
FIG. 28 depicts a cross-sectional view of the layer structure after the removal of exposed top titanium layer in areas opened through the top polyimide.

FIG. 28 shows that the titanium 72*b* top surface layer is removed in the vias by wet etch to leave platinum 73 as the top surface layer in the vias. Typically the preferred titanium is removed at 20° C. to 30° C. for 50 s to 70 s with dilute hydrofluoric acid. The plate is first rinsed in a lower cascade rinse bath for 50 s to 70 s then in a middle cascade rinse bath for 50 s to 70 s and finally in a bubbler cascade rinse bath for 50 s to 70 s. The plate is dried with filtered nitrogen, front side only.

Figure 29:
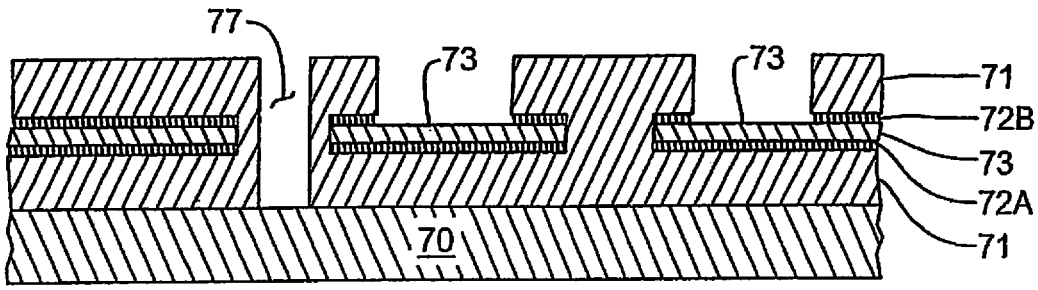
FIG. 29 depicts a cross-sectional view of the layer structure after the singulation of arrays to create individual parts prior to removal from the supporting glass plate substrate.

FIG. 29 shows that the arrays are singulated by cutting through the polyimide 71 layer by laser 77 whereby individual parts are created. The single circuit electrode array is then removed from the supporting glass plate substrate 70 by a solvent.

Figure 30:
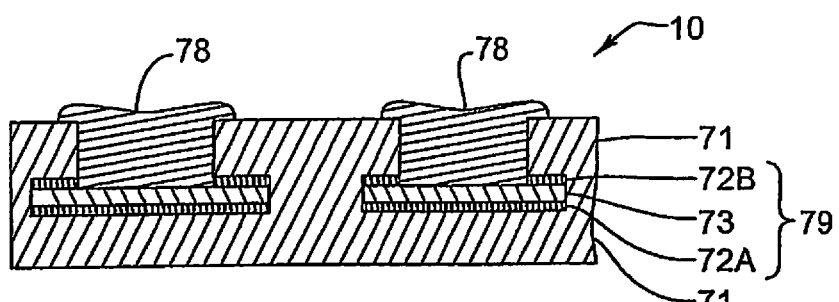
FIG. 30 depicts a cross-sectional view of the layer structure after the deposition of additional material on electrode sites which depicts a part of the flexible circuit electrode array.

FIG. 30 shows that the supporting glass substrate 70 is removed. The vias are electroplated with preferably platinum, most preferably platinum gray 78. The vias are preferably filled with platinum gray 78 are electroplated on the platinum trace 73. Platinum gray is described in US 2003/0192784 "Platinum Electrode and Method for Manufacturing the Same" to David Zhou, the disclosure of which is incorporated herein by reference. The method to produce platinum gray according to the present invention comprises connecting a platinum electrode, the anode, and a conductive substrate to be plated, the cathode, to a power source with a means of controlling and monitoring either the current or voltage of the power source. The anode, cathode, a reference electrode for use as a reference in controlling the power source and an electroplating solution are placed in a electroplating cell having a means for mixing or agitating the electroplating solution. Power is supplied to the electrodes with constant voltage, constant current, pulsed voltage, scanned voltage or pulsed current to drive the electroplating process. The power source is modified such that the rate of deposition will cause the platinum to deposit as platinum gray, the rate being greater than the deposition rate necessary to form shiny platinum and less than the deposition rate necessary to form platinum black.

The electrode region of the array 10 is immersed in this process into sulfuric acid. The electrode region of the array 10 is rinsed under a flow of distilled water for at least 30 s. The plating solution is kept at 21° C. to 23° C. The plating solution is being stirred at 180 rpm to 220 rpm. The electrical contact fixture is loaded into the rotary holder. The electrode end of the array 10 is immersed into plating bath and the apparatus is aligned. The system is allowed to stabilize for 4 min to 6 min. After starting a potentiostat program a pneumatic control timer is started immediately. The array is rotated by 90° every 4 min to 6 min for the duration of plating. After the plating cycle is completed, the electrode region of the array 10 is rinsed under a flow of distilled water for at least 30 s. The array is then removed from the electroplating electrical contact fixture. The entire array is rinsed in a vial with fresh distilled water for up to about 24 hours. The array 10 is then dried in nitrogen.

It becomes apparent especially from FIG. 30 that the electrode 78, preferably platinum gray has a direct contact to the conducting layer 73, preferably platinum. The electrode 78 is slightly slimmer than the trace 72a/73/72b, preferably titanium/platinum/titanium. Polymer 71, preferably polyimide, covers the part of the trace, which does not have a contact with the electrode 73. This part of the trace is covered by titanium 72b. There is a surprisingly strong adhesion between titanium 72b and polyimide 71. The trace 72a/73/72b is referred to in FIG. 30 and subsequently in FIGS. 31-32 simplified as number 79.

Figure 31:
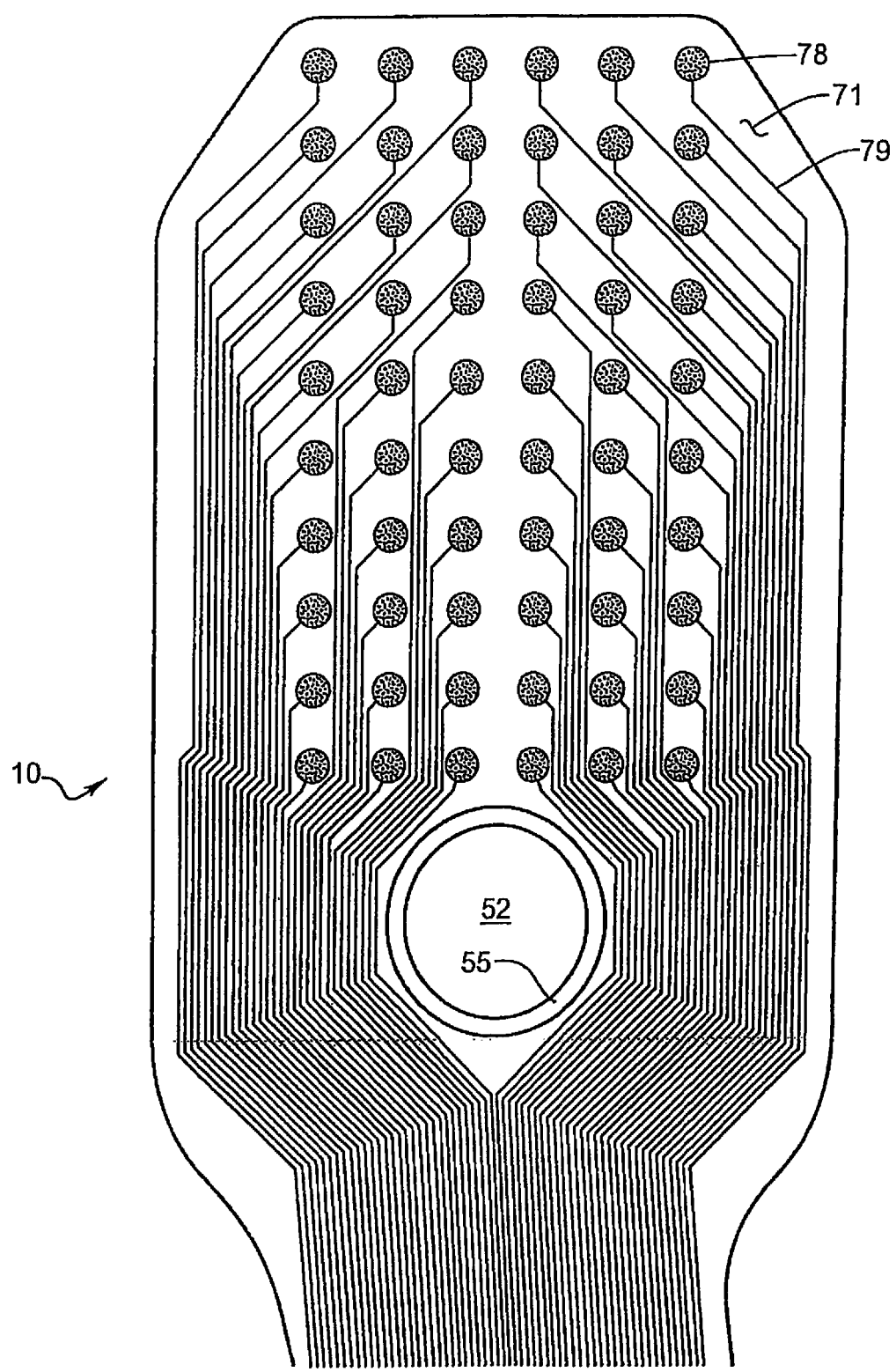
FIG. 31 depicts a top view of the flexible circuit electrode array.

FIG. 31 shows an enlarged top view of the flexible circuit electrode array 10 which is a part of the body 1 as shown for example in FIG. 5. The preferred positions of the electrodes 78 and the preferred wiring by the trace metal 79 both embedded in the polymer 71 are shown in FIG. 31.

Figure 32:
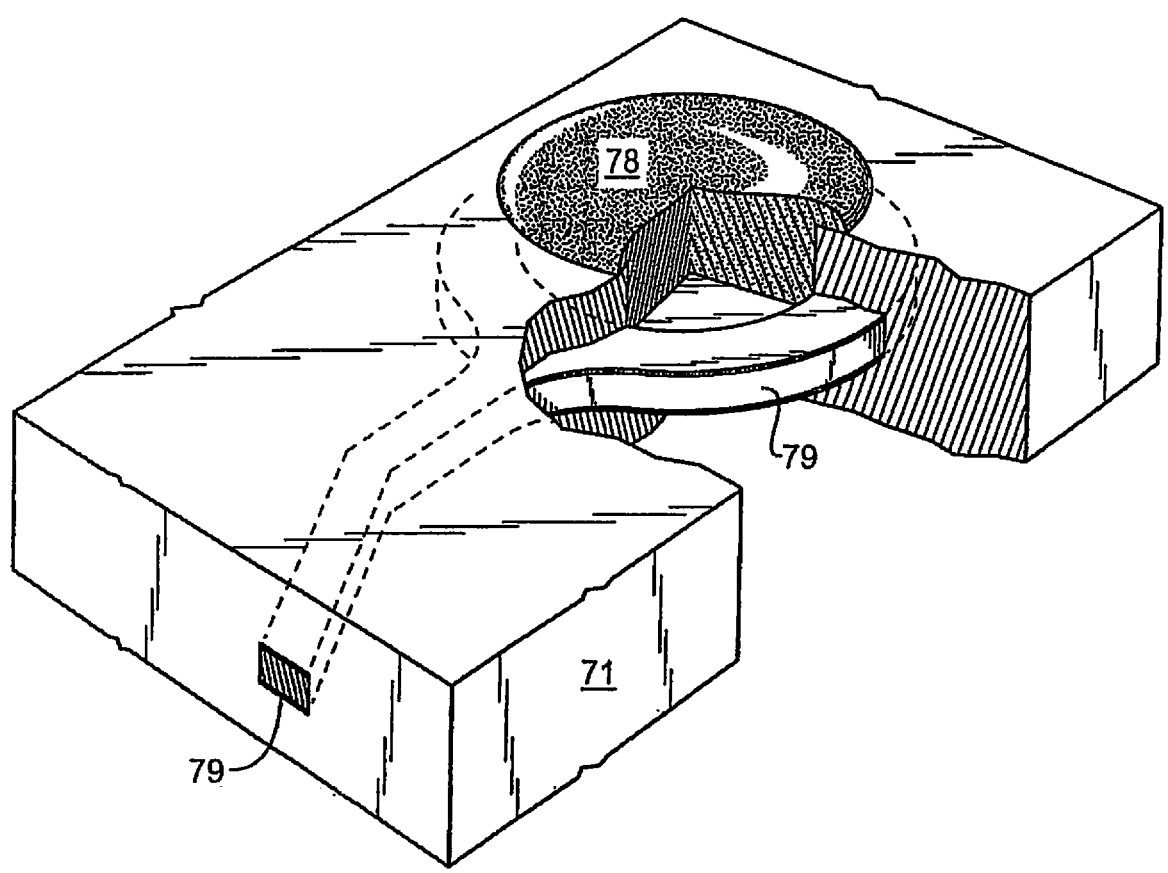
FIG. 32 depicts a perspective view of a part of the flexible circuit electrode array.

FIG. 32 shows a three dimensional view of a part of the flexible circuit electrode array 10. It shows one electrode 78 which has a contact with the trace metal 79. It also shows that the trace metal 79 overlaps the electrode 78 and the electrode 78 overlaps the via in the polymer 71. FIG. 32 further shows the adhesion of the polymer 71 with the trace metal 79 and the electrode 78 which results in a very high effective insulation of the trace metal 79 and the electrode 78. The figure shows also that the trace metal 79 is preferably composed of platinum conducting trace 73 covered on the lower and upper side preferably with a thin titanium layer 72a and 72b. The figure finally shows that the first applied base polymer 71a and the subsequently applied top polymer layer 71b form a single polymer layer 71.

The present invention will be further illustrated by the following examples, but it is to be understood that the invention is not meant to be limited to the details described herein.

Example 1

A 10.2 cm×10.2 cm×0.15 cm supporting glass plate substrate 70 was marked with a batch and plate identification code by mechanical engraving. Then a 5.5 μm thick layer of polyimide BPDA/PDA (derived from 3,3',4,4'-biphenyltetracarboxylic dianhydride (BPDA) and p-phenylendiamine (PDA)) layer 71a was applied onto the front side of the glass plate 70 as a liquid precursor by spin coating and cured to Polyimide, PI2611.

Then a 0.05 μm layer of titanium 72a was applied on the polyimide layer 71a preferably by magnetron sputtering, a 0.5 μm layer of platinum 73 was applied on the titanium layer 72a preferably by magnetron sputtering, and a 0.10 μm layer of titanium 72b was applied onto the layer of platinum 73 preferably by magnetron sputtering yielding a titanium/platinum/titanium thin film stack.

Subsequently a 2 μm layer 74 of positive photoresist AZ 1512 (Microchemicals GmbH, Germany) was applied on the titanium layer 72b. The photoresist layer 74 was irradiated by UV light through a mask whereby a pattern was created. The irradiated areas of the photoresist layer 74 where removed by a developer solution AZ 300-MW (Microchemicals GmbH, Germany). The remaining areas of the photoresist layer 74 masked selectively the areas where metal traces were obtained in the further process.

Titanium from the layer 72b was removed by wet etch, 50:1 Dilute HF (Ashland Chemical), in the exposed areas. Platinum from the layer 73 was removed by wet etch, DI water:HCl:HNO$_3$ in volume ratio 1:3:1, in the exposed areas. Then the residual photoresist layer 74 was removed with a liquid immersion 20 s in acetone and 20 s in isopropanol. Titanium from the layer 72a was removed by wet etch, 50:1 Dilute HF (Ashland Chemical), in the exposed areas. The areas where titanium 72a and 72b and platinum 73 were removed expose polyimide 71 as the surface layer.

The base polyimide surface layer 71a was activated and partially removed by RIE in all areas not covered by trace metal conductors. The surface was treated in 100 mTorr, 85% O$_2$, 15% CF$_4$ for 2 min at 200 W and 20° C. as shown in the following Table 1.

TABLE 1

| | Reactive Iron Etch (RIE) | | | | |
| --- | --- | --- | --- | --- | --- |
| Step | Gases | Pressure [mTorr] | Power [W] | Time [m:s] | Temperature [° C.] |
| Pump Down | — | 1 | 0 | 00:01 | 20 |
| Etch | 85% O$_2$, 15% CF$_4$ | 100 | 200 | 02:00 | 20 |
| Pump Down | — | 1 | 0 | 00:01 | 20 |

The surface was subsequently treated in KOH-deimidization bath at 25° C. for 5 min with manual agitation of the carrier boat at least every 60 s. The surface was first rinsed in a lower cascade rinse bath for 60 s, in a middle cascade rinse bath for 60 s, and finally in a bubbler cascade rinse bath for 60 s. The surface was dried with filtered nitrogen. The surface was then treated in an HCl-deimidization bath at 25° C. for 5 min with manual agitation of the carrier boat at least every 60 s. The surface was first rinsed in a lower cascade rinse bath for 60 s, in a middle cascade rinse bath for 60 s, and finally in a bubbler cascade rinse bath for 60 s. The deimidization process is shown in the following Table 2.

TABLE 2

| | Deimidization | | | |
|---|---|---|---|---|
| Step | Concentration | Pressure [Torr] | Time [m:s] | Temperature [° C.] |
| KOH | 1.0N KOH | 1 | 5:00 | 25 |
| HCl | 1.0N HCl | 1 | 5:00 | 25 |

Then a 5.5 µm thick top layer 71b of a precursor solution was applied by spin coating and cured to Polyimide, PI2611 on the top of base polyimide 71a. Polyimide 71a and 71b combined to polyimide 71 after curing.

Then an adhesion promoter, VM652, and aluminum foil, P/N X11652-1.518 (All Foils Inc) were applied by magnetron sputtering on top of the polyimide layer 71 yielding 1.0 µm mask aluminum thin film 75.

Then a 12 µm layer of positive photoresist 76, AZ P4620 (Microchemicals GmbH, Germany) was applied on the aluminum layer 75. The photoresist layer 76 was irradiated by UV light through a mask whereby a pattern was created. The irradiated areas of the photoresist layer 76 were removed by a developer AZ 1:1 (Microchemicals GmbH, Germany) [Developer: DI Water]. The removed areas of the photoresist layer 76 exposed selectively the areas where vias were obtained in the further process.

Aluminum 75 was removed in exposed areas by wet etch, sulfuric acid, 1.0 N (0.5 M). The polyimide surface layer 71 was removed by RIE in all areas not masked by aluminum. Then the residual photoresist layer 76 was removed from the aluminum layer 75 by immersion 20 s in acetone and 20 s in isopropanol. Vias were created with titanium 72b as the top surface layer in the vias. Then the aluminum mask layer 75 was removed from the polyimide 71 layer by wet etch. The titanium 72b top surface layer was removed in the vias by wet etch, 50:1 Dilute HF (Ashland Chemical), to leave platinum 73 as the top surface layer in the vias.

The arrays were singulated by cutting through the entire polyimide 71 layer by laser to create individual parts prior to removal from the supporting glass plate substrate 70. The array 10 was removed from the supporting glass substrate 70.

The electrodes were electroplated with platinum gray 78. The plating solution contained 18 mM $(NH_4)_2PtCl_6$ dissolved in 0.46 M $Na_2HPO_4$. The electrode vias were filled with platinum gray 78, which was in contact with the platinum trace 73.

Example 2

Example 2 was carried out according to example 1 with the difference that the base polyimide surface layer 71a was activated and partially removed by RIE in all areas not covered by trace metal conductors. The surface was treated in 100 mTorr, 85% $O_2$, 15% $CF_4$ for 2 min at 200 W and 20° C. as shown in the preceding Table 1 and the deimidization was omitted. The adhesion strength between the base polyimide layer 71a and the top polyimide layer 71b is shown in Table 3. Table 3 shows the measurement of two adhered dry polyimide films (DRY) and two adhered polyimide films kept in saline solution for 7 days at 87° C.

TABLE 3

| | | | Adhesion Strength | |
|---|---|---|---|---|
| Ex | RIE | Deimidization | Polyimide - Polyimide Adhesion Strength [N] Dry | Polyimide - Polyimide Adhesion Strength [N] Wet |
| 1 | 85% $O_2$, 15% $CF_4$ | | 3.0 | 2.4 |

Example 3

Example 3 was carried out according to example 1 with the difference that the base polyimide surface layer 71a was activated by deimidization. The surface was subsequently treated in KOH-deimidization bath at 25° C. for 5 min with manual agitation of the carrier boat at least every 60 s. The surface was first rinsed in a lower cascade rinse bath for 60 s, in a middle cascade rinse bath for 60 s, and finally in a bubbler cascade rinse bath for 60 s. The surface was dried with filtered nitrogen. The surface was then treated in an HCl-deimidization bath at 25° C. for 5 min with manual agitation of the carrier boat at least every 60 s. The surface was first rinsed in a lower cascade rinse bath for 60 s, in a middle cascade rinse bath for 60 s, and finally in a bubbler cascade rinse bath for 60 s. The deimidization process is shown in the following Table 2 and the RIE was omitted. The adhesion strength between the base polyimide layer 71a and the top polyimide layer 71b is shown in Table 4. Table 4 shows the measurement of two adhered dry polyimide films (DRY) and two adhered polyimide films kept in saline solution for 7 days at 87° C. (WET).

TABLE 4

| | | | Adhesion Strength | |
|---|---|---|---|---|
| Ex | RIE | Deimidization | Polyimide - Polyimide Adhesion Strength [N] DRY | Polyimide - Polyimide Adhesion Strength [N] WET |
| 1 | | KOH, HCl | 2.1 | 2.0 |

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A flexible circuit comprising:
   a flexible polymer base layer forming an electrode portion, a cable portion, and a bond pad portion, the bond pad portion adapted to connect to an electronic control unit;

a patterned metal layer including layers of base titanium, platinum and top titanium, on the flexible polymer base layer, including at least one electrode pad, at least one bond pad and at least one trace connecting the electrode pad to the bond pad, the patterned metal layer including a base coating layer, conducting layer, and a top coating layer;

a flexible polymer top layer deposited on the flexible polymer base layer and the patterned metal layer, including at least one opening, smaller than the electrode pad, to expose the electrode pad;

the top coating layer defining an opening aligned with the opening in the flexible polymer top layer;

an electrode plated directly on the conducting layer of the electrode pad through the top coating layer and the flexible polymer top layer and overlapping the flexible polymer top layer, wherein the electrode pad overlaps the opening in the flexible polymer layer, and the electrode overlaps the flexible polymer layer such that the flexible polymer layer is between the electrode and electrode pad; and wherein there is no boundary between a top surface of the flexible polymer base layer and the flexible polymer top layer so that the flexible polymer base layer and flexible polymer top layer form a flexible polymer single layer, due to the top surface of the flexible polymer base layer and the flexible polymer top layer being cured together.

2. The flexible circuit according to claim 1, wherein the flexible polymer base layer and flexible polymer top layer are polyimide and curing is imidizing the polyimide.

3. The flexible circuit according to claim 1, further comprising a soft polymer layer, softer than the flexible polymer single layer, over at least a portion of the flexible polymer single layer.

4. The flexible circuit according to claim 1, further comprising at least one bumper bonded to a peripheral edge of the flexible circuit.

* * * * *